United States Patent [19]

Kolber et al.

[11] Patent Number: 4,942,303
[45] Date of Patent: Jul. 17, 1990

[54] COMPUTER CONTROLLED FLUOROMETER DEVICE AND METHOD OF OPERATING SAME

[75] Inventors: Zbigniew Kolber, Shoreham; Paul Falkowski, Stony Brook, both of N.Y.

[73] Assignee: Associated Universities, Inc., Washington, D.C.

[21] Appl. No.: 304,273

[22] Filed: Jan. 31, 1989

[51] Int. Cl.$^5$ .............. G01N 21/64; G01N 21/62; G01N 21/63; G01N 21/00
[52] U.S. Cl. .............. 250/458.1; 250/459.1; 250/461.1; 250/461.2; 356/417
[58] Field of Search ........... 250/458.1, 459.1, 461.1, 250/461.2; 356/317, 318, 417; 436/172

[56] References Cited

U.S. PATENT DOCUMENTS

| | | | |
|---|---|---|---|
| 3,666,945 | 5/1972 | Früngel et al. | 356/318 |
| 4,178,512 | 12/1979 | Früngel et al. | 250/461.1 |
| 4,293,225 | 10/1981 | Wheaton et al. | 250/461.1 |
| 4,650,336 | 3/1987 | Moll | 356/317 |
| 4,698,308 | 10/1987 | Ikeda | 250/461.2 |
| 4,730,922 | 3/1988 | Bach et al. | 356/317 |
| 4,786,813 | 11/1988 | Svanberg et al. | 250/461.2 |
| 4,802,768 | 2/1989 | Gifford et al. | 356/318 |
| 4,804,849 | 2/1989 | Booth et al. | 250/459.1 |
| 4,804,850 | 2/1989 | Norrish et al. | 356/417 |
| 4,840,485 | 6/1989 | Gratton | 356/317 |

OTHER PUBLICATIONS

Falkowski, et al., "Relationship of Steady-State Photosynthesis to Fluorescence in Eucaryotic Algea", Biochimica et Biophysica Acta 849, (1986) pp. 183-192.
Kolber, et al., "A 'Pump and Probe' Fluorometer", Biowatt News, No. 9, Nov. 1987, pp. 4-5.

*Primary Examiner*—Constantine Hannaher
*Assistant Examiner*—Edward J. Glick
*Attorney, Agent, or Firm*—Margaret C. Bogosian

[57] ABSTRACT

A computer controlled fluorometer device and method of operating same, said device being made to include a pump flash source and a probe flash source and one or more sample chambers in combination with a light condenser lens system and associated filters and reflectors and collimators, as well as signal conditioning and monitoring means and a programmable computer means and a software programmable source of background irradiance that is operable according to the method of the invention to rapidly, efficiently and accurately measure photosynthetic activity by precisely monitoring and recording changes in fluorescence yield produced by a controlled series of predetermined cycles of probe and pump flashes from the respective probe and pump sources that are controlled by the computer means.

14 Claims, 11 Drawing Sheets

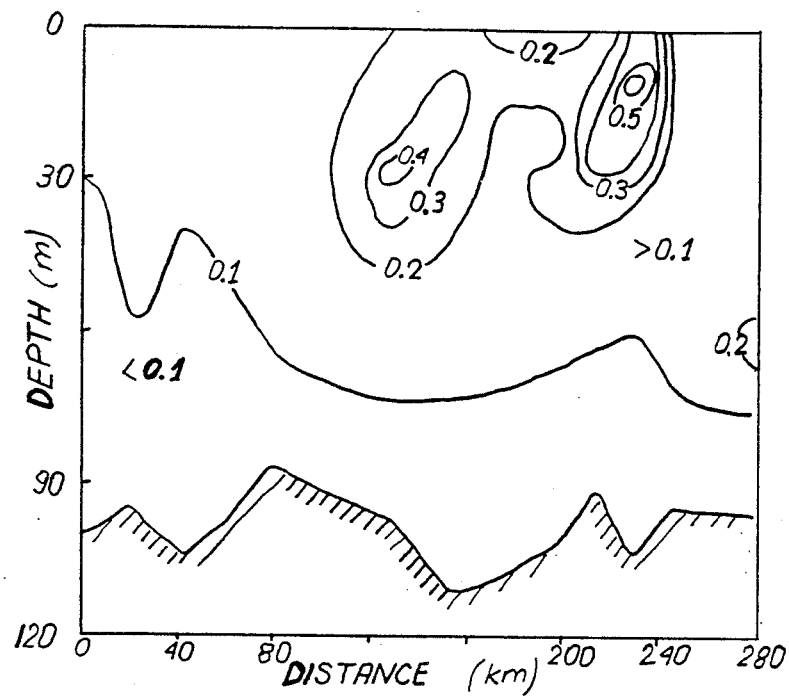
Fig.13
CHLOROPHYLL (µg/l)
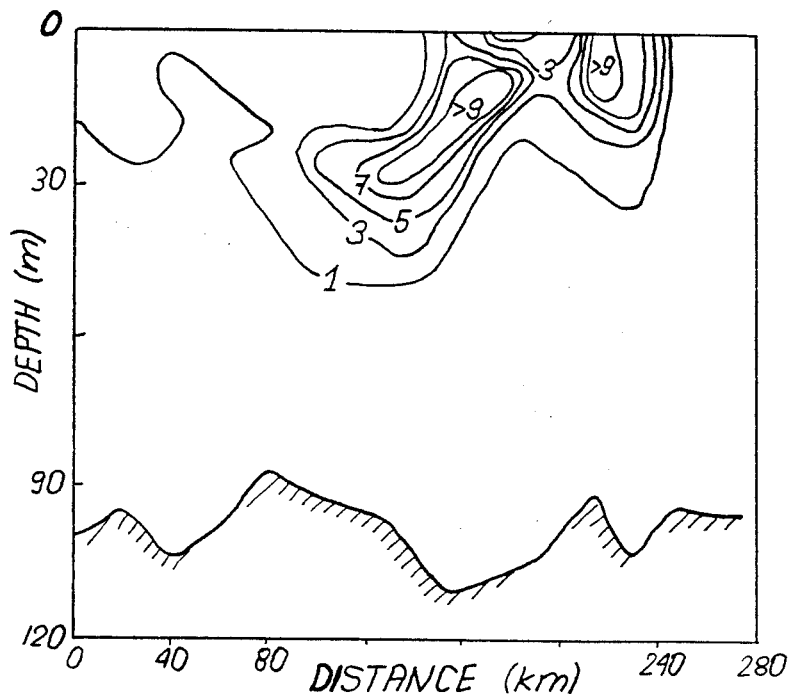

COMPUTER CONTROLLED FLUOROMETER DEVICE AND METHOD OF OPERATING SAME

This invention was made with Government support under contract number DE-AC02-76CH00016, between the U.S. Department of Energy and Associated Universities, Inc. The Government has certain rights in the invention.

BACKGROUND OF THE INVENTION

There are a variety of methods practiced for measuring changes in fluorescence yield under varying light intensities. Different kinds of fluorometer devices have been developed to implement such methods. One such known method is to use the so-called "pump and probe" technique in which the change in fluorescence yield of a relatively low intensity probe flash is measured following a pump flash which is usually made intense enough to saturate the observable effect. An example of one type of known fluorometer device that uses a steady source of light from a lamp in combination with a flash of light to bring about transient fluorescence is described in U.S. Pat. No. 4,650,336, which issued Mar. 17, 1987. While that device makes it possible to take certain desirable measurements of plants, as do other known prior art fluorometers, there remains a need for more accurate and readily usable fluorometer devices to provide such desired measurements.

A primary object of the present invention is to provide a programmable, computer controlled fluorometer device that is operable to readily provide a number of different measurements of photosynthetic activity, by means of precisely following changes in fluorescence yield of relatively weak probe light, preceding and succeeding a stronger actinic pump flash of light.

Another object of the invention is to provide a conveniently portable and submersible version of such a fluorometer device to enable the taking of such measurements from submerged plants and phytoplankton.

Yet another object of the invention is to permit such an operable fluorometer device to use programmable commands, readily variable pump and probe flash intensities and increments, and readily variable delays in sequences of pump and probe flashes, in order to afford measurement of maximum fluorescence yields, optical absorption cross sections, and turnover times of photosynthetic samples under either darkness or ambient irradiance conditions.

Still another object of the invention is to provide a fluorometer device that can independently measure cross sections and turnover times of photosynthetic organisms under their normal ambient conditions, such as in undersea environments.

A further object of the invention is to enable measurement of such photosynthetic parameters of plants and phytoplankton as level of variable fluorescence, absorption cross-section of Photosystem II, turnover time of photosynthesis, and estimation of the energy transfer among the Photosystem II units. Additionally, the invention will enable measurement of the on-going photosynthetic production rates under ambient light conditions.

Yet another object of the invention is to provide a submersible instrument that enables the same measurements to be done in situ, in the ocean. Additionally, application of the device should allow estimation of the relative growth rates of phytoplankton.

Additional objects and advantages of the invention will become apparent from the description of the invention that is presented below.

SUMMARY OF THE INVENTION

The disclosed preferred embodiment of a fluorometer instrument comprises two sources of excitation light, four detector channels, a data acquisition module, and a single board computer. One of the excitation lights provides a short "pump" flash of an intensity that is controlled from zero to the level of saturation of Photosystem II. The second light source provides a "probe" flash of an intensity that is attenuated to 0.5% of the saturating pump flash. Detector channels are used to measure the fluorescence signal, intensity of the pump and probe flashes, and intensity of the ambient Photosynthetic Active Radiation (PAR) present in the sunlight irradiance. The data acquisition module is used for conditioning of the detector signals and converting them to a digital form. The submersible version of the disclosed fluorometer also accommodates signals from associated temperature and depth sensors. A single-board computer controls the operation of the fluorometer, stores the data in its internal memory, and performs desired data analysis. The device will be further described in reference to FIG. 1.

The instrument of the invention, because of the special design of the signal conditioning unit, allows measurement at chlorophyll concentration as low as 0.05 $\mu g/l$.

The instrument of the invention, because of using the cylindrical mirror around the sample chamber, allows significant (up to five times) reduction in the required energy of the pump and the probe flash.

The instrument of the invention, because of using the beam splitter in the optical design and the two chamber concept, allows simultaneous measurement of the phytoplankton photosynthetic parameters, both in the dark and when exposed to the light.

The method of the the invention, described in section 3d, below, allows measuring of the photosynthetic production rates of plants and phytoplankton in situ in the ocean. It allows an instant profiling of the production rates along the water column. The 14C method, as an alternative to the disclosed method, requires about 6 hours of incubation and can be done only for discrete, bottled samples. Additionally, the bottled phytoplankton is cut off from the nutrient flux and experiences different intensity and spectral quality of the light. The other method, using a passive fluorescence sensor (Biospherical), cannot account for the variability in the photosynthetic potential of the phytoplankton (variability of $\Delta\phi_{sat}$ in the range of 0.3 to 1.8), cannot account for quenching effects that can modify the fluorescence yield by as much as 300%, cannot account for the presence of the pheopigment, and requires the assumptions that the absorption cross section of photo system II (PSII) is constant along the water column, and the turnover time for photosynthesis does not change with irradiance. The two last assumptions are wrong.

The method of the invention described in section 3e, allows measuring of the phytoplankton relative growth rate and monitoring the nutrient status of the phytoplankton.

DESCRIPTION OF THE DRAWINGS

FIG. 13 is two charts that illustrate a comparison between relative growth rate of phytoplankton as estimated with the method of the subject invention, and the chlorophyll concentration as recorded in the Gulf of Maine.

DESCRIPTION OF A PREFERRED EMBODIMENT

Figure 1:
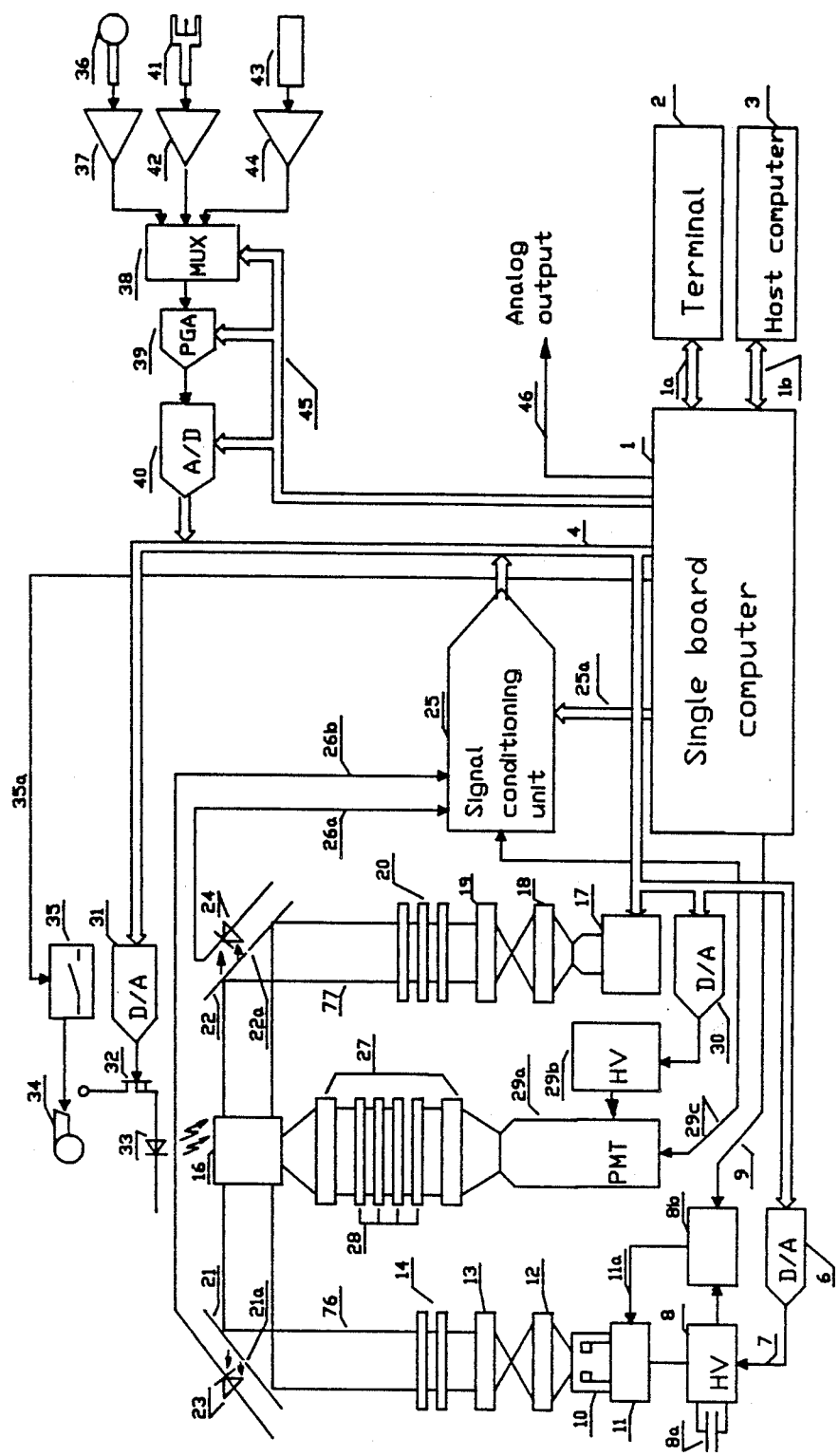
FIG. 1 is a schematic circuit diagram of a computer controlled fluorometer device constructed and arranged according to the invention.

In the preferred embodiment illustrated in FIG. 1, the energy of a pump flash is controlled by associated software. A microprocessor in the form of a single-board computer (SBC) 1 is controlled by program software, which is more fully described in sub-section A, Control Program, below. SBC 1 is operatively connected by a conventional multi-conductor cable 1a to a conventional computer operator's terminal 2, and by a second cable 1b to a host computer 3 that is operable to process and store measurement data. Further description of all of these computer related components of the disclosed device is given below, in sub-section 1. The digital signal representing the energy of the pump flash is sent from a suitable commercially available computer means including the microprocessor or single board computer (SBC) 1, which has a memory, via a data and address bus 4 to a digital/analog converter (D/A) 6. An appropriate D/A converter for the applications of the preferred embodiment should feature a C-MOS technology for low power consumption and digital interface that allows a direct connection to be made to the processor bus 4. Such converters are commercially available, e.g. as either 7226 or 7528 type from either Analog Devices or Precision Monolithic Corps. The analog representation of the pump flash energy is sent to a high voltage power supply 8 on a conductor wire 7. A suitable high voltage power supply for this use can be designed by one skilled in the art as a voltage controlled fly-back voltage converter, or may be purchased from such vendors as EG&G (model PS-350), or Del Electronics Corp. (model PMS 1—1). The high voltage converter 8 charges a storage capacitor 8a to a voltage V that is proportional to the analog signal present on wire 7. The capacitance of the storage capacitor should be in the range 1 to 2 $\mu$F, and have a voltage rating in the range 1.5 to 2 kV. The energy E stored in the storage capacitor is given by the expression $E=0.5CV^2$. A storage capacitor specially designed for the pulse discharge application of the preferred embodiment can be purchased from either High Energy Corp., CSI Capacitors, or DEL Electronics Corp.

The storage capacitor 8a discharges through a xenon flashlamp 10, which results in a short, strong flash. The flashlamp with a suitable socket 11 can be purchased from EG$\mu$G (preferred model 12B1.5, socket FY-904), or from Hamamatsu (preferred model L2453, socket E2454). At maximum flash energy corresponding to about $2\times10^{15}$ quanta cm$^{-2}$ the half-peak duration of the pump flash is about 1.6 $\mu$sec. The timing of the pump flash is controlled by a timer (not shown) included in the SBC by sending a short, 2 $\mu$sec. pulse on wire 9 to the flashlamp triggering circuit 8b, which can be designed by one skilled in the art using a thyristor as a switching device, or by using the triggering circuit in an EG&G PS-350 power supply. The preferred embodiment of the disclosed submersible fluorometer employs the first solution, in order to satisfy the smaller space requirements. The triggering pulse is sent to the flashlamp socket on wire 11a.

Figure 3:
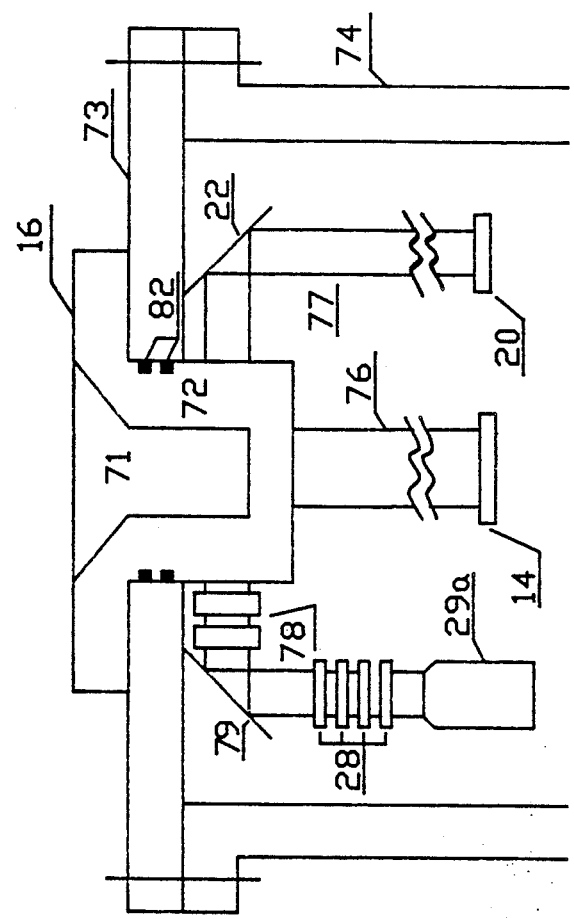
FIG. 3 is a schematic circuit diagram that illustrates a windowed sample cavity for use in connection with the type of device illustrated in FIG. 1, and illustrated in relation to input beam means and output beam detectors.

After the light from the flashlamp is collected by a suitable condenser 12, it is collimated by a conventional collimating lens 13, and then passes a set of conventional excitation filters 14. The condenser 12 can be designed by one skilled in the art using a set of short focal length lenses. In the disclosed fluorometer the condenser is built from three short focal length lenses with a 45 mm outside diameter. The first lens is an aspheric one. The collimating lens is a double convex one. Lenses are commercially available from Edmund Scientific Co. The excitation filter 14 is a combination of the Corning 4-76 and 4-96 glass filter. The collimated blue-green light is bent 90 degrees by a flat first surface mirror 21, and then hits a sample chamber 16. The first surface mirror is available from Edmund Scientific Co. In a preferred embodiment of the fluorometer the sample chamber contains a glass cuvette (not shown). In the submersible embodiment of the disclosed fluorometer the sample chamber (16) is designed in the form of a cylindrical window 72 with a cavity 71 in the center (FIG. 3).

The source 17 of the probe flash may be designed in essentially the same way as the pump flash, by using a high voltage power supplier, storage capacitor, and a xenon flashlamp (which are not individually shown, but are used in source 17). Alternatively the probe flash may be provided by a set of blue light emitting diodes (type LDB5410 from Siemens), or by a solid-state laser diode emitting in the range of 900–1200 nm (nanometers) with frequency doubling. When the flashlamp is used, the condenser 18 and collimation lens 19 that are fed from the probe flash source 17 are the same types as those used with the pump beam. A set of probe beam excitation filters 20 is made from Corning 4-76 and Corning 4-96 filter elements, and from two sharp cut-off interference filters blocking light wavelengths above 550 nm. The interference filters can be purchased from Corion, type LS-550F. The probe beam is bent 90 degrees by a first surface mirror 22 and hits the sample chamber 16 on the side thereof opposite to the entrance for the pump beam.

The intensities of the pump and probe flashes are monitored, by photodiodes 23 and 24, respectively, placed behind the mirrors 21 and 22, and are exposed to a fraction of the excitation beams through pinholes 21a and 22a, respectively, scratched on the surfaces of the mirrors. Suitable photodiodes can be purchased from Hamamatsu, EG&G, or United Detector Technology. The photodiode used in the disclosed fluorometer is Hamamatsu S2386-5K. The signals from the photodiodes 23 and 24 are delivered to the signal conditioning unit 25 using shielded cables 26b and 26a, as shown in FIG. 1.

Fluorescence light that is emitted from a selected specimen or test sample (not shown) in the sample chamber 16 is collected by the condenser lens system 27, then passes through a system of emission filters 28, and strikes a fluorescence detector 29a. The condenser lens system 27 is built from a set of conventional aspheric and plano-convex lenses and can be easily assembled by one skilled in the art. The emission filters 28 consist of two 670 nm cut-off filters, type LG670 from Corion, arranged in series with two 685 nm bandpass interference filters from MicroCoatings, Inc. The detector used (29a) includes a photomultiplier (PMT) with a photocathode of the multi-alkali type, which has high quantum efficiency at 685 nm. In one preferred model of the disclosed fluorometer a Hamamatsu R2066 PMT was used. In the submersible model of the disclosed device a miniature type Hamamatsu R1463 PMT was used. In the preferred embodiment, illustrated in FIG. 1, the high voltage for the photomultiplier is provided by a Hamamatsu C2456 subminiature modular power supply 29b (HV). The gain of the photomultiplier is controlled by varying the high voltage from the HV power supply 29b in the range of 650–1100 volts, using the voltage control input in power supply 29b. The controlling voltage in the range 0 to 1.5V is provided by a digital to analog converter 30 (D/A) (Analog Devices AD7226). The signal from the photomultiplier 29a is delivered to the signal conditioning unit 25 by a shielded cable 29c. For good noise performance this cable should be as short as possible.

The preferred embodiment of the fluorometer is equipped with a PAR sensor 36. The sensor can be designed by one skilled in the art and using a photodiode with a blue interference bandpass filter, or may be purchased from Biospherical, Inc. The signal from the PAR sensor is processed by a conventional current-/voltage converter 37, based on an Analog Devices AD515 amplifier featuring 0.075 PA bias current. The output voltage signal from converter 37 is multiplexed by suitable multiplexer 38 (MUX) (Analog Devices AD7501), then amplified and sampled in the programmable gain amplifier 39 (PGA) based on Analog Devices AD365, and converted to the digital form by an A/D converter 40 (Analog Devices AD7572).

The preferred embodiment of a submersible version of the fluorometer is also equipped with a commercially available submersible temperature sensor 41 and a depth sensor 43. The temperature sensor used is a Sea Bird model SB3-01/F. The signal from the temperature sensor is converted from frequency to voltage using Analog Devices ADVFC32 frequency to voltage converter 42, and is then processed in a way similar to that used to process the PAR signal (from 36). The depth sensor 43 used is a DS-500 model from Data Instruments. The current loop signal from the depth sensor is converted to voltage signal using converter amplifier 44 (OP 27 from Analog Devices or Precision Monolithic), and is then processed by a method similar to that used for processing the temperature signal. The operations of the PAR, temperature, and depth measurements are controlled by timing and gain control signals from the SBC 1 on line 45, connected as shown in FIG. 1.

The disclosed fluorometer is equipped with a software programmable source of background irradiance. The digital representation of the background irradiance signal is transmitted from SBC 1 over line 4 and is converted to an analog form in the D/A converter 31 (type AD7226 from Analog Devices). The output signal from that D/A converter controls a current source 32, which drives a light emitting diode 33. The background irradiance emitted by the diode 33 [or a set (not further shown) of such light emitting diodes, in given embodiments] is directed into the top of the sample chamber 16, as is indicated by the wavy lines over chamber 16, in FIG. 1. The spectral quality of the background irradiance can be controlled by providing several sections of the current source 32 with suitable conventional diodes that emit light of different colors. Thus, a set of diodes (not shown) could be used (for 33). The current source can be designed by one skilled in the art, using a MOSFET, HEXSense type power transistor, the preferred type being IRCZ24 from International Rectifier.

The disclosed fluorometer is also equipped with a circuit for controlling a peristaltic pump 34 which allows measurements in a flow-through system. The circuit uses a solid-state relay 35 of a type commercially available from Teledyne or National Control Corp. The solid-state relay is controlled by a digital signal from the SBC 1, which is transmitting to it on line 35a.

Figure 2:
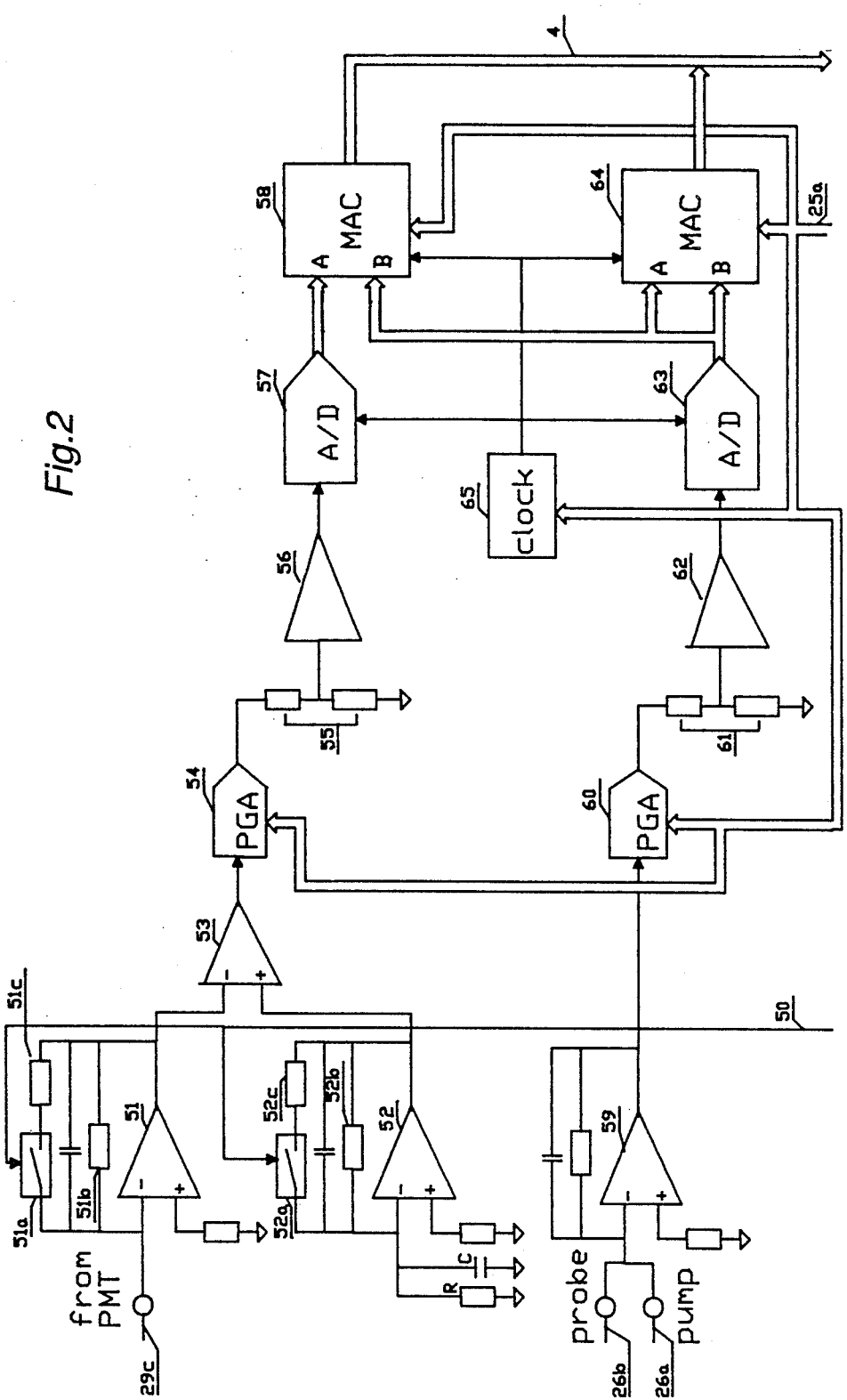
FIG. 2 is a schematic circuit diagram of the signal conditioning unit subcircuit shown in FIG. 1.

The role of the signal conditioning unit 25 is to accommodate the signal from photodetectors 23, 24, and 29a, and to convert these signals to digital form. The operation of the signal conditioning unit is controlled by SBC 1 through control line 25a. A schematic block diagram of the unit 25 is shown in FIG. 2. In the fluorescence part of the unit two matched operational amplifiers, 51 and 52 (FIG. 2), are used. In the preferred embodiment a type OP-17 amplifier, by Analog Devices or Precision Monolithic, is used. The input of amplifier 51 is connected to the output of the photomultiplier (PMT) 29a at a terminal line 29c. The input of amplifier 52 is connected through a conventional resistor R and capacitor C, as shown, to ground, and the positive terminals of both amplifiers 51 and 52 are similarly grounded through suitable resistors as shown. A pair of analog switches 51a and 52a, respectively, shunt through 10K ohm resistors (51c and 52c) the 1 Megaohm resistors 51b and 52b when a pump flash is present. This results in a low voltage/current gain by amplifier 51, which prevents its over-saturation during the pump flash. The type of analog switch used in the preferred embodiment is an ADG202A switch from Analog Devices. The switches 51a and 52a are reopened 30 μs after the pump flash, thereby increasing the current/voltage gain to a level that allows detection of the fluorescence yield from a sample during a low intensity probe flash. The operation of switches 51a and 52a is controlled by a timing signal from SBC 1 on wire 50.

A side effect of the opening of switches 51a and 52a is a charge insertion to the input of amplifiers 51 and 52, which results in a voltage transient at their outputs. These voltage transients, because of their low bandwidth at switch-off condition, have a long decay time. As a result there will be a sum of the transient and the probe signals in the output of amplifier 51. Amplifier 52, however, will show only the presence of the transient signal. By matching the switches and their associated RC parameters in amplifier 52 to the output resistance and capacitance of the photomultiplier 29a, the transient signal on both amplifiers will be the same. This common signal is later cancelled in the amplifier 53 (which is an Analog Devices type OP-27) by subtracting the signal of amplifier 52 from the signal of amplifier 51. The amplifier 53 is followed by a variable gain amplifier (PGA) 54 in order to accommodate a wide dynamic range of the fluorescence signal. The type of variable gain amplifier 54 used in the preferred embodiment is AD526, from Analog Devices. The gain of the amplifier 54 (and that of PGA, 60) is controlled from SBC 1 over line 25a.

Next the signal is attenuated by a resistive divider circuit 55, amplified by an amplifier 56 and converted to digital form by a flash A/D converter 57. The amplifier 56 should have a very large bandwidth and high output current in order to properly drive the flash A/D converter. The type used in the disclosed fluorometer is a CLC401 from Comlinear Corp. The choice of the flash A/D converter should satisfy the required conversion speed, resolution, and power consumption for a selected application. In the disclosed circuit a CA3306C from RCA is used for the converter 57, which features a 15 MHz conversion rate, 6 bit resolution, and about 80 milliwatts/active of power consumption. The conversion rate is controlled by a conventional clock generator 65, which can be easily designed by one skilled in the art. The digital signal from converter 57 is supplied to the input A (in FIG. 2) of a Multiplier and Accumulator (MAC) 58. Both MAC 58 and a similar MAC 64 are type LMA1009 from Logic Devices, Inc. in the preferred embodiment.

The signal from diodes 23 and 24 (which appear on lines 26b and 26a at the pump and probe energy monitoring terminals shown in FIG. 2) are processed through amplifier 59 in a way similar to that used to process the fluorescence signal, with the only difference being that the amplifier 59 does not require switched gain. The pump and probe monitoring signals are supplied through variable gain amplifier (PGA) 60, resistive divider 61, amplifier 62, and A/D converter 63 to the input B of the MAC 58; and to both inputs A and B of MAC 64. The two MAC's are programmed over control lines 25a. Depending on the desired system requirement, either of the two different modes of operation may be employed. In the first mode, streams of data from the flash converters are accumulated in the MAC's (64 and 58) output registers. As a result, the input signal is digitally integrated. The integration process assures that the energy, not just the amplitude, of the measured signals is recorded. In the second mode, the MAC's are programmed to store the cumulative product of signals on their inputs A and B. Accordingly, the operation of the MAC 58 is described as $$Kfp = \sum_i f(i)\, p(i)$$

and the operation of MAC 64 is described as $$Kpp = \sum_i p(i)\, p(i),$$

where signals f(i) and p(i) are, respectively, the digital representations of the fluorescence and excitation signals during the i-th conversion. The Kfp and Kpp signals are sent to the SBC 1 through a data bus 4, where the division of Kfp and Kpp yields a Kf signal, where $$Kf = \frac{\sum f(i)\, p(i)}{\sum p(i)\, p(i)}.$$

The Kf signal is then the result of the least squares fit of the fluorescence signal to the probe excitation signal, with the amplitude of the fluorescence signal as the sought parameter. As the probe excitation signal on photodiode 24 (FIG. 1) is several orders of magnitude larger than the fluorescence signal, it is practically noise-free and can be used as a pattern for the fluorescence signal.

The disclosed procedure enables a 5- to 10-fold increase in the signal to noise ratio in case of low chlorophyll concentration in the range of 0.05 to 0.5 $\mu$gram/liter. A simpler signal conditioning unit based on peak detection of the Photodiode and photomultiplier signals and direct analog/digital conversion, using a conventional A/D converter, can be easily designed by one skilled in the art. In such a solution use of a charge-sensitive amplifier instead of the standard current conversion in the fluorescence channel is preferred. Charge-sensitive amplifiers feature low noise and fast recovery from over saturation (in the preferred embodiment, a model A-225 from Amptek may be used). Such a solution, however, will suffer from lower signal to noise ratio, especially at low chlorophyll concentration, and it will suffer from inappropriate representation of the pump and probe flash energy.

The design of the sample chamber 16, used in the preferred embodiment of the submersible version of the fluorometer, was determined by the desired pressure-resistant cylindrical form of the underwater housing. Details of the sample chamber design are shown in FIG. 3. The chamber 16 has a cylindrical cavity 71 formed in a round window 72 that is made from a conventional translucent cast acrylic material. The window is fitted to a hole in the endcap 73 of a suitable conventional underwater housing 74 and is sealed by a set of two 0-rings 82. The probe beam 77, passing through filter 20 (also see FIG. 1), is bent 90 degrees by the first surface mirror 22 and enters the sample chamber 16 through the side of window 72. The pump beam 76 enters the sample chamber 16 through its bottom wall (being different in this respect from the arrangement shown in FIG. 1), after passing through filter 14. It should be understood that for the embodiment shown in FIG. 3, the fluorescence beam leaves the sample chamber from its left side. After being collimated by a set of two cylindrical lenses 78 (available from Melles Griot), the fluorescence beam is bent 90 degrees by a first surface mirror 79, then it passes the set of emission filters 28 and strikes the photomultiplier 29a. The location of the fluorescence exit port on the side of the sample chamber is essential for the proper measurement of the fluorescence yield signal under sunlight irradiance. The fluorometer operates in a vertical position, with its cavity 71 in the sample chamber facing upward, as shown in FIG. 3. An alternative location of the fluorescence exit port, for example at the bottom of the cavity 71 in the sample chamber, would result in an excessive amount of red light from the sun as compared to the fluorescence signal induced by the probe beam. This, in turn, would limit both the dynamic range of the fluorescence signal and the signal-to-noise ratio. In the present device, the parallel configuration of the pump, probe, and fluorescence beams is essential in order to enable the double flash fluorometer to be fitted into a desirably small submersible housing (e.g., housing 74). Another advantage is that by forming the sample chamber with a cavity 71, the preferred embodiment allows a single window to interface the two excitation beams and the emission beam to the outside environment.

Figure 4:
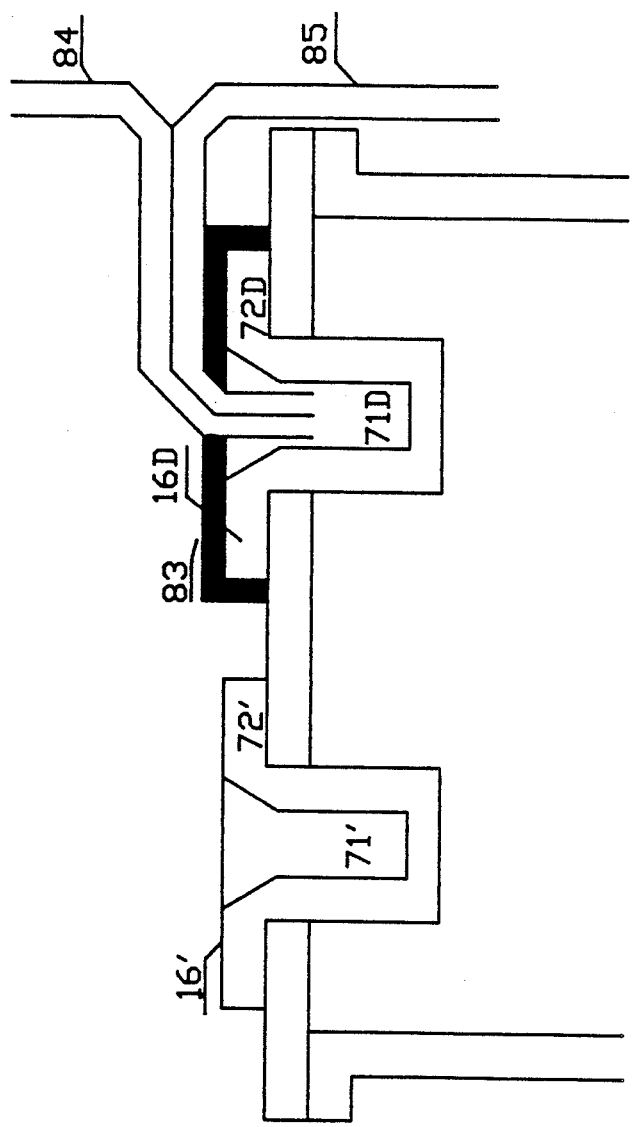
FIG. 4 is a schematic side elevation planview of a portion of an alternative embodiment of the inventive device shown in FIGS. 1 and 3, wherein a dual-windowed sample-cavitied configuration of the invention is depicted.

A submersible embodiment of the disclosed fluorometer can be outfitted, if desired, with a second sample chamber (the chamber 16D) for conducting fluorescence measurements in the dark. The design of such a double-chamber fluorometer is partially depicted in FIG. 4. A dark sample chamber 16D is made similar in construction to the open chamber 16', except that its plastic window 72D is covered with an opaque cap 83 through which two pieces of pipe 84 and 85 are fastened by suitable conventional means. One end of both pipes extends into the cavity 71D of sample chamber 16D, as shown. Both pipes are bent 90 degrees so they are parallel to the surface of the endcap 83, and pipe 84 is bent 90 degrees to extend upward, while pipe 85 is bent 90 degrees to extend downward relative to chamber 16D. When the fluorometer is lowered down the water column (downcast operation), water enters the sample chamber through the pipe 85, and leaves the sample chamber through the pipe 84. During an up-cast operation, the flow of the water is reversed. The length of the pipes and their curvatures determines the level and time of the dark adaptation with respect to the speed of the downcast and up-cast.

Figure 5:
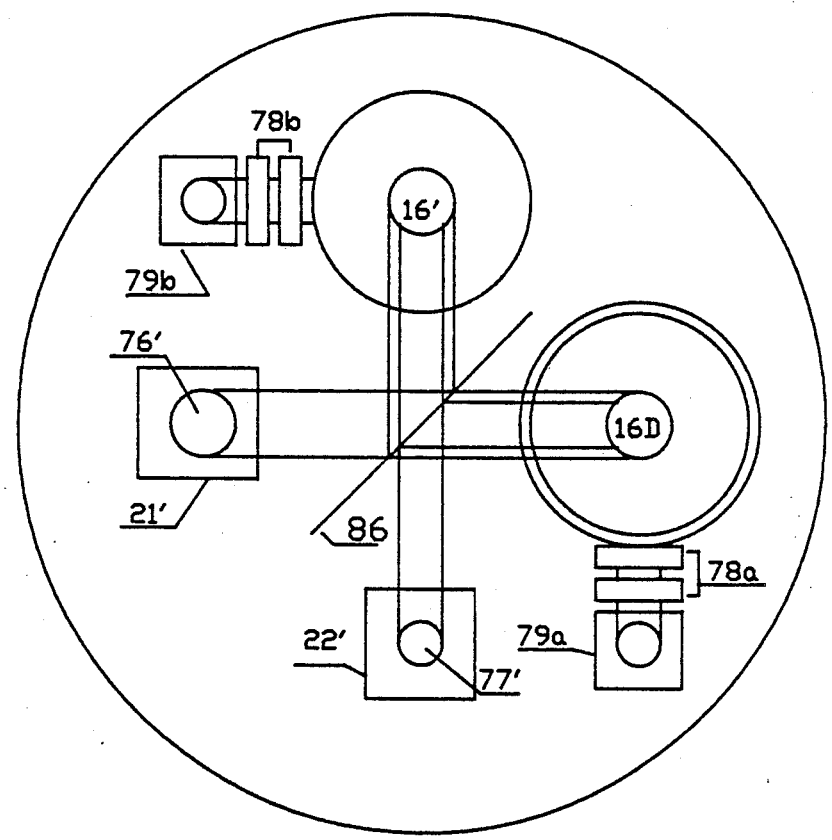
FIG. 5 is a schematic top plan view of the dual-windowed and double-cavitied alternative embodiment of the invention illustrated in FIG. 4.

The optics for the double chamber configuration of the disclosed fluorometer is designed in such a way that both chambers 16' and 16D share the pump flash source and probe flash source, seen in FIG. 5, which can be analogous to the flash lamp 10, and the probe light source 17 in the embodiment illustrated in FIG. 1. Both the probe beam 77' and the pump beam 76' (FIG. 5) are bent 90 degrees from the direction parallel to the fluorometer housing cylindrical axis by the first surface mirrors 22' and 21', respectively. Next, both beams strike a conventional beamsplitter 86. The beamsplitter reflects 50% of impinging incoming light and transmits the remaining 50% through its surface. As a result, the beams hitting the open chamber 16' and dark chamber 16D contain 50% of the original pump beam 76' and 50% of the original probe beam 77'. The fluorescence beams leave the sample chambers from the side, next they are collimated by sets of cylindrical lenses 78a and 78b, then are bent 90 degrees by set of the first surface mirrors 79a and 79b, and after filtering are detected by a pair of photomultipliers.

Figure 6:
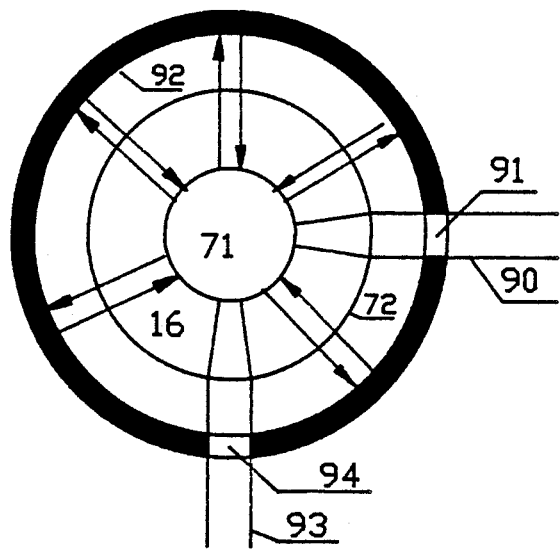
FIG. 6 is a top plan view of the window and sample cavity shown in FIG. 3.

The sample chamber 16 (or chambers, 16' and 16d) in the submersible embodiment of the disclosed fluorometer is surrounded by a cylindrical aluminum mirror 92, as shown in FIG. 6, with an opening formed therein to define an excitation port 91 and another opening therein to define an emission port 94. An excitation beam 90, after entering the excitation port 91, is directed toward the cavity 71 at the center of the sample chamber 16 due to a focusing effect of its cylindrical wall 72. A fraction of the photons in the excitation beam 90 is absorbed by the phytoplankton; however, most of them leave the sample chamber without inducing any photosynthetic effect. At a chlorophyll concentration of 1 $\mu$gram/liter the fraction of absorbed photons can be as small as $1\times10^{-7}$. The mirrored wall 92 directs the leaving photons (outward pointing arrows, in FIG. 6) back to the sample chamber, as shown by the inward pointing arrows, thus increasing the efficiency of light utilization in the excitation beam. This efficiency increasing feature of the invention enables lower power consumption in the submersible version of the disclosed fluorometer, and causes lower RF noise levels to be induced by the pump and probe flashes. Optionally, this feature allows the employment of blue light emitting diodes as a source of the probe flash.

A. Control Program

The operation of the double flash fluorometer is supervised by the on-board microprocessor SBC (1) (See FIG. 1), and is completely controlled by the software run on the computer. The single-board computer (SBC) 1 is commercially available in STD bus standard, from such vendors as Prolog, Ziatech, Micromint, or WinSystem, or in G-64 (STE) bus standard from Gespac. The choice of a suitable processor, memory capacity, speed, and software tools required for a given desired application can be easily determined by those skilled in the art. Preferably, the SBC (1) should feature a C-MOS technology for a low power consumption, DOS compatibility for easy programming, and small physical dimensions for easy packaging into a submersible enclosure (STD, or STE standard). The SBC should also contain a set of programmable timers, either as a separate chip (HD63B40, from Hitachi), or as an integral part of the processor chip (V-20 or V-50 from NEC). Also the SBC should contain an interrupt controller, and battery backup for C-MOS RAM memory. A submersible version of the disclosed device is equipped with the Winsystem MCM-SBC8, V-20 based single-board computer; whereas a non-submersible version of the disclosed instrument is equipped with a Micromint BCC52, 8052AH based single-board computer. Both feature serial ports for interfacing with an operator's terminal 2, and a host computer 3. The terminal is used for pre-programming a variety of desired series of experiments and the host computer is used for processing and storing the measurement data. In the submersible version the serial ports are accessed through an underwater connector in the submersible housing.

The choice of the software tools for programming the SBC is determined by the type of SBC (1) used. The control program for the non-submersible version of the disclosed fluorometer has been written in Basic-52 (a firmware is contained in a 8052AH chip within the SBC); the program for the submersible version of the fluorometer has been written in a ROMable version of Aztec C. A printout of the program code in BASIC is disclosed in section C, followed by the claims. The source C code for controlling the submersible version of the fluorometer is structurally identical to the BASIC program. Both programs are menu-driven and allow easy pre-programming of the fluorometer by a person who need not have extensive programming skills.

B. Operation of the Fluorometer

The disclosed double flash fluorometer operates in a way that enables it to measure the extent of changes of the fluorescence yield of photosystem II (PSII) in response to a pump flash. Application of the pump flash leads to a charge separation in a fraction of the reaction centers, and to transient reduction of the primary electron acceptor, called QA. The reduced OA is then oxidized at a rate corresponding to the speed of the electron transfer along the PSII and photo system I (PSI) electron transport chain. If another photon will be absorbed during the time period when QA stays reduced, then the excess of the excitation energy will be dissipated in the form of fluorescence, thereby increasing the apparent yield of the fluorescence. The difference in the fluorescence yield before and after the pump flash depends on the average state of the reaction centers before the pump flash, and on the energy of the pump flash. The average state of the reaction centers before the pump flash depends on the level of photosynthetic activity of PSII that is induced by the background irradiance. This in turn is a function of the intensity of the background light, and the efficiency of light collection by PSII. The pump light will activate an additional fraction of the reaction centers. The higher the energy of the actinic pump flash and the efficiency of light collection, the bigger is this fraction. Ultimately, with the pump flash strong enough, all the reaction centers will be closed, and the fluorescence yield will reach its maximum value, Fs.

The fluorescence yield of PSII can be measured as the ratio of the fluorescence signal to the excitation signal under the condition that the excitation signal itself will not change the state of the reaction centers. This defines a probe flash: the integrated number of excitation photons emitted during the probe flash must be small enough that no reaction centers will be hit more than once. This corresponds to the condition that the probe flash energy be kept below 1% of the energy of the saturating pump flash, and that the time of the probe flash exposition be shorter than the time constant of $QA^-$ oxidation, which is about 160 $\mu$sec. In the disclosed device the energy of the probe flash is kept below 0.5% of the energy of the saturating pump flash, and the half-peak duration of the probe flash is made to be about 0.7 $\mu$sec.

Figure 7:
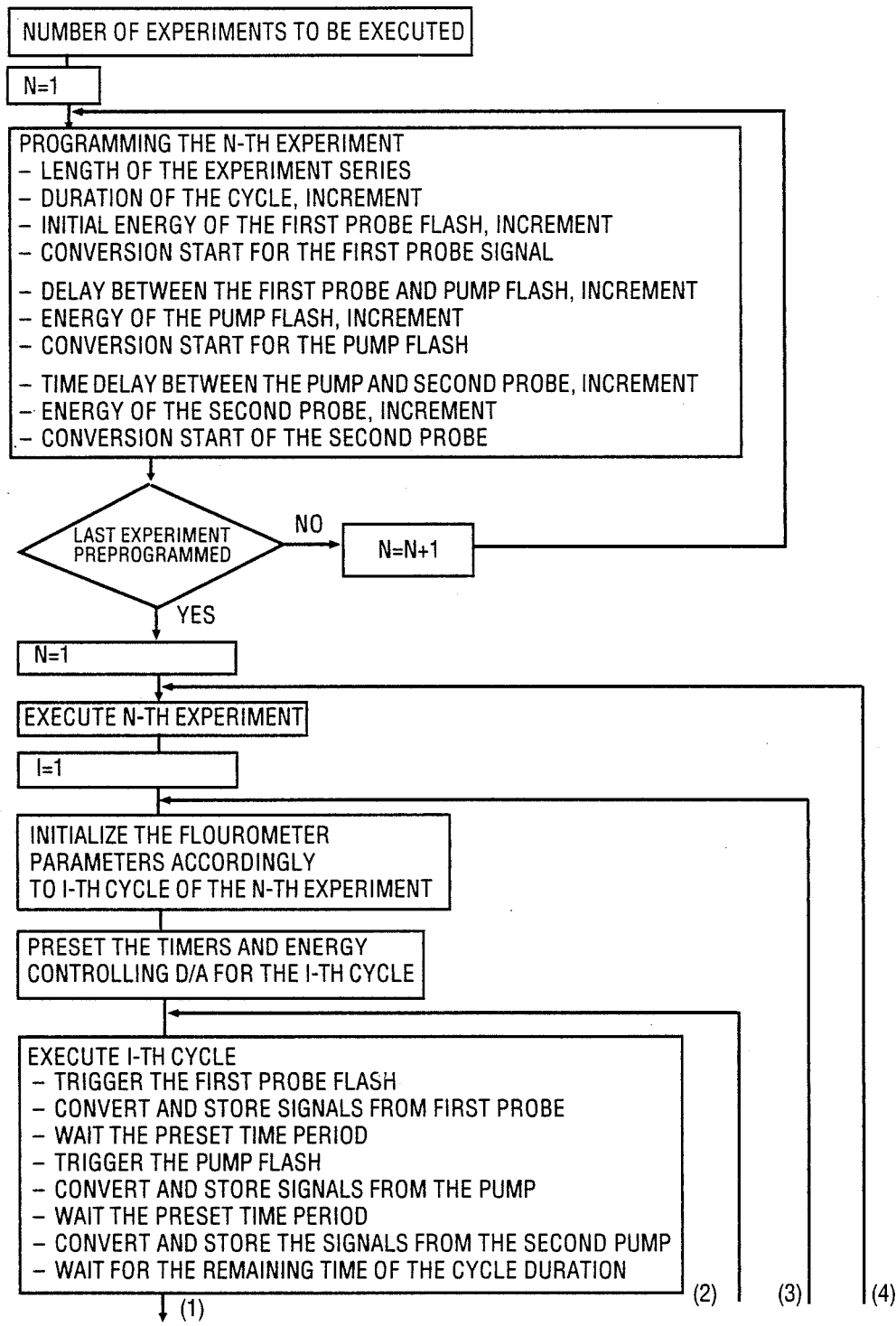
FIGS. 7 and 8 are matching parts of a flow diagram chart of the operation of the fluorometer device of the invention.
Figure 8:
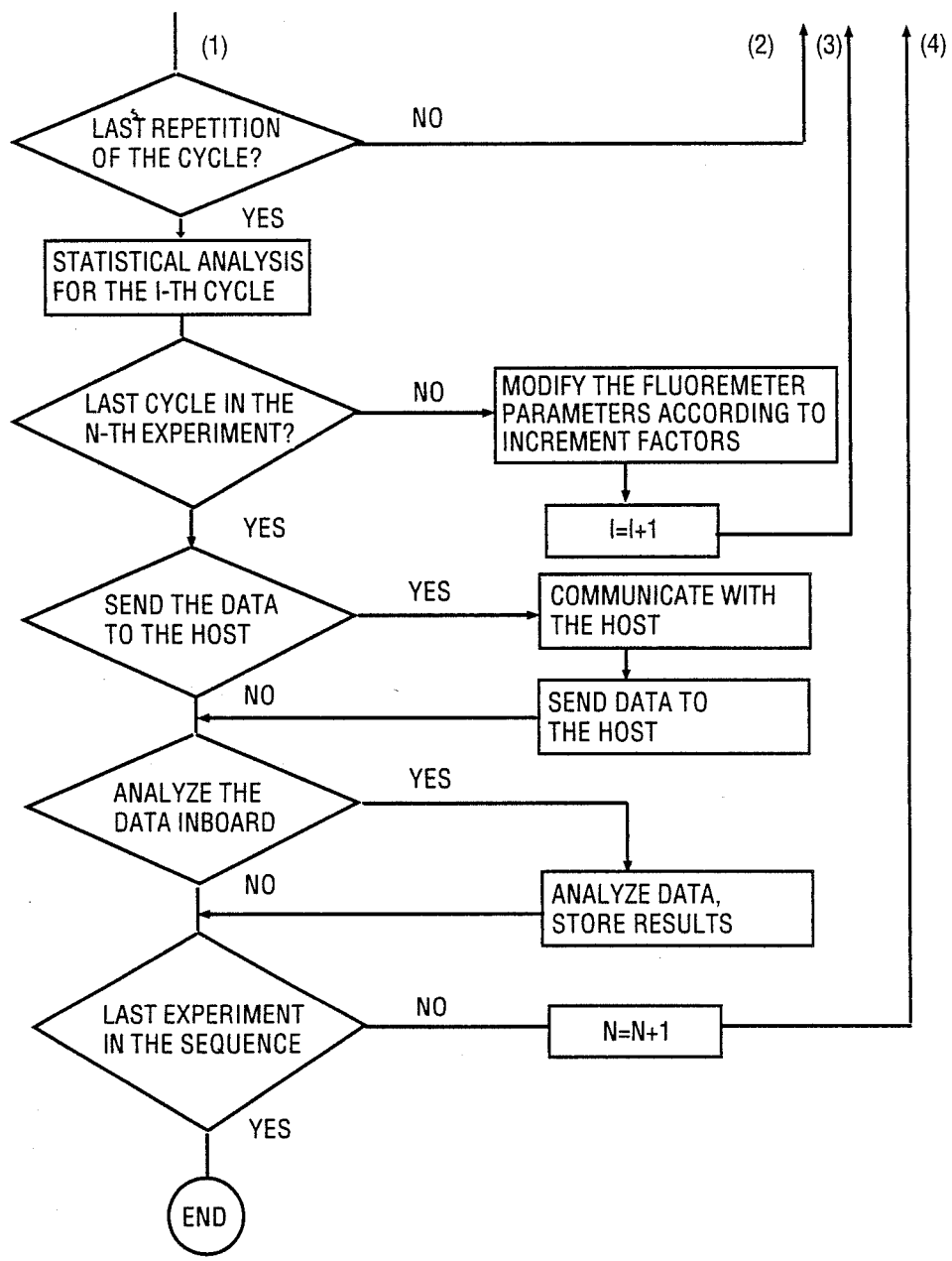

Varying the intensity of the pump flash, the sequence of the probe and pump flash, and the time delay between the pump and probe flashes, a number of parameters describing the photosynthetic performance of the plants and phytoplankton can be measured with the disclosed device. A flow-chart of the fluorometer operation is described in FIGS. 7 and 8. The numbered lines at the bottom of FIG. 7 and at the top of FIG. 8 diagram the interconnections between these two parts of the flow chart. The steps and text of the flow chart are self explanatory. In a general case, the fluorometer operation is pre-programmed as a sequence of experiments. Every experiment consists of a predetermined series of the probe/pump cycles of pre-programmed length. Every cycle may consist of any desired combination of the probe and pump flashes. The inventors have found that for many of their applications the most frequently used is a probe-pump-probe cycle. In such a case the cycle parameters are as follows:

cycle duration energy of the first probe flash, together with increment factor, describing if the energy of the first probe flash should change from cycle to cycle in the series, the amplitude of required change, and if the change should be linear or logarithmic time delay between the first probe flash and the pump flash, together with the increment factor energy of the pump flash with increment factor time delay between the pump flash and the second probe flash with increment factor energy of the second probe flash with the increment factor.

The increment factors are a convenient way of pre-programming the instrument operations in experiments, such as taking measurements of the decay kinetics of PSII, measurements of the absorption cross section of PSII or, in some kinetics experiments, requiring on-fly modification of the fluorometer parameters. The fluorometer operation pertaining to different types of experiments is described below in sections 3a through 3e.

3a. Measurement of the Variability of the Fluorescence yield, $\Delta\phi_{sat}$ The range of the variability of the fluorescence yield, $\Delta\phi_{sat}$, is a measure of the photosynthetic potential of the plants and phytoplankton. It is defined as a relative difference of the fluorescence yield in a state when all reaction centers are closed (Fs), and in a state when all reaction centers are open (Fo):

$$\Delta\phi_{sat} = \frac{Fs - Fo}{Fo}.$$

This parameter depends on the nutrient status of photosynthetic organisms, and is also affected by such stress factors as herbicides and low/high temperature. The experiment is made on a dark adapted sample, and is pre-programmed in such a way that a sequence of three flashes is generated. First, there is a probe flash, during which the amplitude of the minimal fluorescence yield, Of is recorded. Next, several milliseconds later, the pump flash at a saturating intensity is applied. The saturating pump flash closes all the reaction centers for the subsequent 50 to 70 $\mu$sec. During this period of time another probe flash is being applied. This time the measured yield of fluorescence corresponds to its maximum level, Fs. In cases of low chlorophyll concentration, such as in the range (0.1 to 0.5 $\mu$g/liter), the cycle of the probe-pump-probe flashes can be preprogrammed to repeat several times, with on-line calculation of data statistics.

Figure 9:
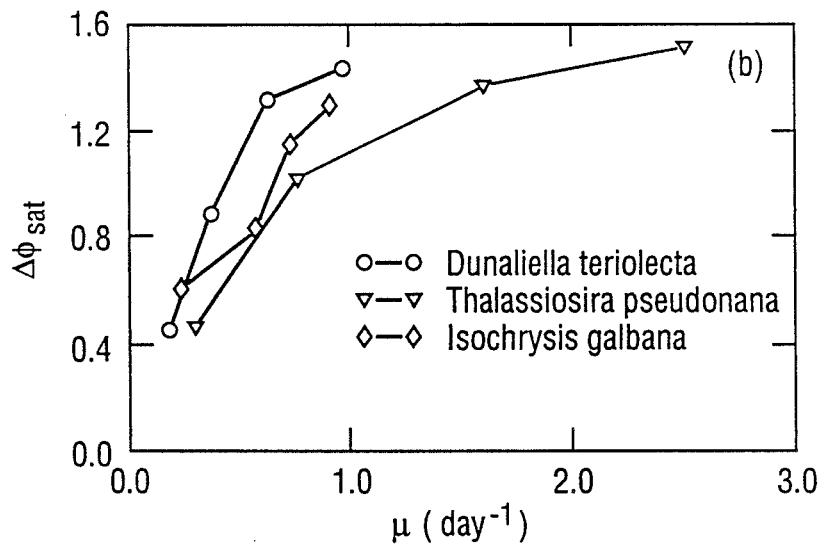
FIG. 9 illustrates an example of the relation between $\Delta\phi_{sat}$ and the growth rate for three species of marine phytoplankton, which are named in this Figure.

For healthy, nutrient-replete phytoplankton cells the $\Delta\phi_{sat}$ reaches levels in the range 1.5 to 1.7, depending on the species. For nutrient-replete cells, the $\Delta\phi_{sat}$ decrease to 0.4 depending on the extent of the nutrient starvation. Also, the phytoplankton growth rate, p, expressed as a number of cell divisions per day, decrease with nutrient starvation. An example of the relation between $\Delta\phi_{sat}$ and growth rate for three species of marine phytoplankton is presented in FIG. 9; the three species are named in FIG. 9.

3b. Measurement of the Absorption Cross Section of the Photosystem II

The efficiency of light collection for photosynthesis is characterized by absorption cross section of the photosystem II, $\sigma$(PSII). The absorption cross section is a geometrical parameter describing the effective area of the reaction center as a target for the photon flux.

This parameter is species dependent, and varies according to the light and nutrient adaptation of photosynthetic organisms. In plants, the σPSII also depends on the stage of development of the organism. From the molecular point of view the σ(PSII) is determined by the molecular size and pigment composition of the light harvesting complex (LHCII) serving the reaction center.

The measurement of σPSII consists of a series of probe-pump-probe flash cycles. The delay between the pump flash and the second probe flash is kept fixed at 50 to 70 μsec. During the series the intensity of the pump flash is gradually increased from cycle to cycle, starting from zero and ending at saturation level. Correspondingly, the fluorescence yield after the pump flash rises from its minimum value, Fo, at zero pump energy, to $F_s$ at saturating pump energy. The shape of the saturation curve of the fluorescence yield follows, with some exceptions, Poisson statistics:

$$\Delta\phi(I)/\Delta\phi_{sat} = 1 - \exp(-I \cdot \sigma PSII),$$

where I is the energy of the pump flash, and $\Delta\phi(I)$ is the variable fluorescence yield induced by the pump flash of energy I. The σPSII can then be calculated by least squares fitting the experimental saturation curve to the above expression, with σPSII and $\Delta\phi_{sat}$ being the searched parameters. The σPSII experiment provides a better estimate of the $\Delta\phi_{sat}$ than does the procedure described in 3a above because it is based on all of the saturation curve of fluorescence yield, instead of on only a single data point.

The theoretical function describing the saturation curve for the fluorescence yield can be modified by adding a parameter describing the probability of energy transfer among PSII units. Fitting the experimental saturation curve of fluorescence yield to such modified function yields a measure of the energy transfer probability.

In case of low chlorophyll concentration, every cycle can be repeated several times for the same pump intensity, thereby improving the signal to noise ratio. The length of the series, the increment of the pump energy, and the number of repetitions for a given cycle are preprogrammed from the menu-driven program. Upon completion of the experiment all the data are stored in the internal RAM memory and may be transferred to the host computer. The fit operation can either be done in the fluorometer single-board computer (SBC) or, more effectively, in the host computer (3).

Figure 10:
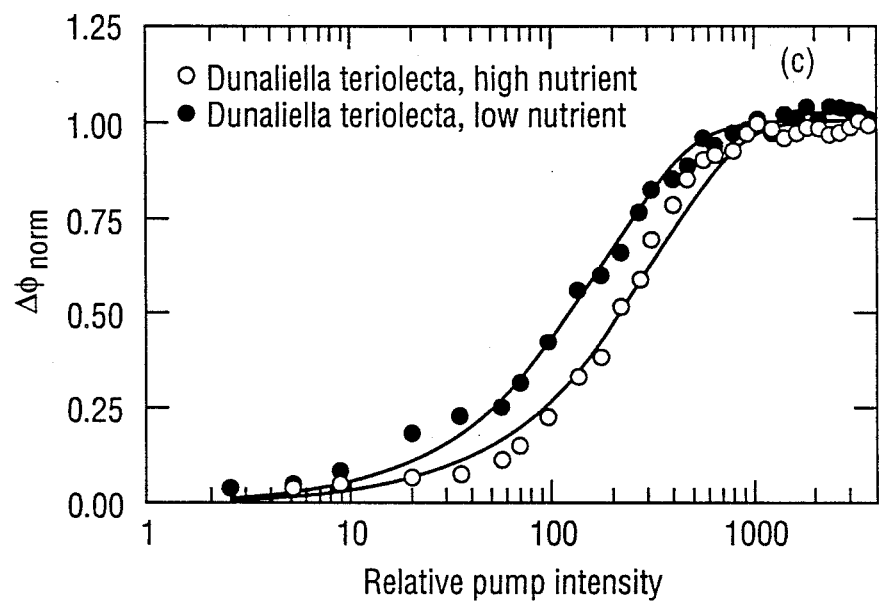
FIG. 10 illustrates experimental data obtained with the subject invention, plotted for saturation curves of fluorescence yield.

The absorption cross section usually increases when plants or phytoplankton adapt to low irradiance levels or to depleted nutrient conditions. On the molecular level this corresponds to an increase in the size of the light harvesting complex and an increase in the abundance of the chlorophyll b or chlorophyll c, relative to chlorophyll a. The probability of the energy transfer between PSII units decreases with nutrient reductions. It also decrease with background irradiance, probably because of the increased level of phosphorylation of light harvesting complex. The experimental saturation curves of fluorescence yield are presented in FIG. 10, which illustrates high and low nutrient conditions.

3c. Measurement of the Decay Kinetics of the Fluorescence

Yield

The decay kinetics of Photosystem II provide information on the rate of electron transport along PSII. The process of the electron transport consists of several redox reactions involving various electron carriers. This results in a multiphasic process of oxidation of QA. Accordingly, the decay kinetics of fluorescence yield following the pump flash can be interpreted in terms of three exponential components in the dark, and four exponential components under ambient light. The time constant of the exponential components correspond to the rates of reduction/oxidation of electron carriers in PSII. The relative amplitudes of the components provide information on the pools of the electron carriers. Analysis of the decay kinetics allows identification of the rate limiting step in photosynthesis, and estimation of the overall turnover time for the photosynthesis.

The measurement of the decay kinetics of the fluorescence yield with the disclosed device is afforded by a series of the probe-pump-probe flash cycles. In making this measurement, intensity of the pump flash is kept at the saturating level, and the delay between the pump and the second probe is gradually increased starting from 50 μsec. The fluorescence yield measured by the second probe flash decreases in proportion to the time delay between the pump and probe flash. The experimental data are then fit to a multiexponential function $$\Delta\phi(t) = \sum_i \alpha_i \cdot \exp(-t/t_i),$$

where $\alpha_i$ is the amplitude of the i-th component, $t_i$ is the time constant of the i-th componant, and t is the time delay between the pump and the second probe flash.

In case of low chlorophyll concentration every cycle can be repeated several times for the same delay between the pump flash and the second probe flash, thereby improving the signal to noise ratio. The length of the series, the increment of the time delay between the pump and the second probe flash, and the number of repetitions for a given cycle is preprogrammed, as desired for a given experiment, from the menu-driven program. Upon completion of the experiment, all the data are stored in the internal RAM memory and may be transferred to the host computer. The fit operation can either be done in the fluorometer single board computer 1 or, more effectively, in the host computer 3.

Figure 11:
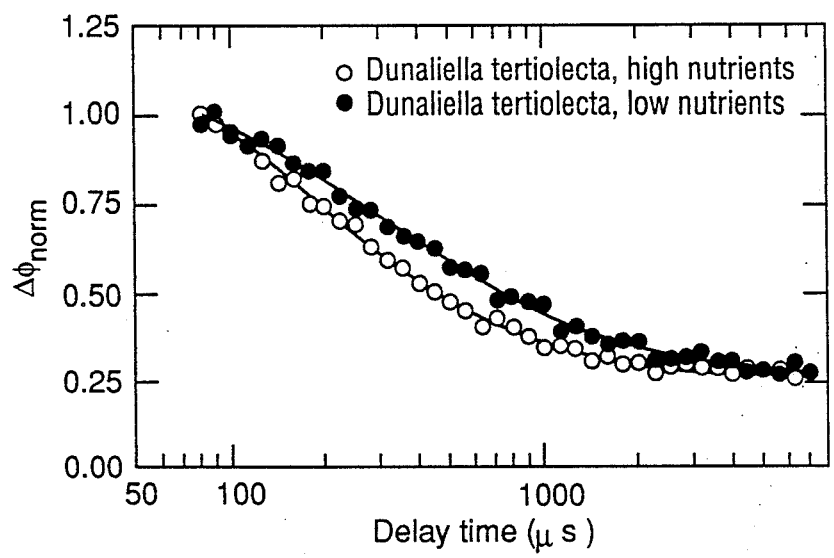
FIG. 11 illustrates example curves of the decay kinetics of fluorescence yield achieved with the preferred embodiment of the invention.

The decay kinetics of variable fluorescence in marine phytoplankton species measured in the dark shows three components. The shorter one, in the range 140–170 μsec corresponds to the oxidation of $QA^-$ in $QA^- QB$ complexes, where QA is the primary electron acceptor, and QB is the secondary electron acceptor. A medium component, in the range of 600 to 800 μsec, corresponds to the process of $QA^-$ oxidation, requiring the prior association of $QA^-$ and QB. A long component, in the range of 100 to 300 msec, corresponds to the rate of back reaction from $QA^-$. Under ambient light the relative amplitude of the long component decrease drastically, and another component of time constant 1.6 to 4 msec appears. This component presumably corresponds to the rate of PQ pool reduction/oxidation. Example curves of the decay kinetics of fluorescence yield achieved with the disclosed device are Presented in FIG. 11.

3d. Measurement of the photosynthetic rates under ambient irradiance.

In the disclosed method, the photosynthesis rate Rphot is assumed to be proportional to the rate of charge separation Rc, yield of electron transport from the primary electron acceptor QA to the plastoquinone pool PQ, Yt, and yield of photochemistry Yp.

$$Rphot = k \cdot Rc \cdot Yt \cdot Yp. \quad (1)$$

The rate of charge separation is assumed to be proportional to the reaction center hit rate $Hr = I \cdot \sigma PSII$, and to the probability that the reaction center is open, A:

$$Rc = Hr \cdot A = I \cdot \sigma PSII \cdot A. \quad (2)$$

The probability of the reaction center being open is estimated from the fluorescence signals:

$$A = (Fs - Fp)/Fs - Fo). \quad (3)$$

The range of variability of fluorescence yield, Fs $-$Of, is measured as described in 3a above. The signal Fs$-$Fp can be estimated from the same measurement made under the ambient light.

The yield of electron transport Yt depends on the rate of the charge separation, Rc, and the turnover of the water splitting enzyme, $t_s$ $$Yt = \frac{1/t_s}{Rc + 1/t_s} \quad (4)$$

The turnover time of the water splitting enzyme $t_s$ determines the ratio of electrons on QA$-$ forced to back-react with P680+ (oxidized form of the special pair of chlorophyll forming the reaction center) in the situation when the electron donor Z remains oxidized at high rates of charge separation, comparable to the rate of Z+ reduction.

The yield of photochemistry Yp depends on the turnover time of photochemistry $t_p$, and on the size of the plastoquinone pool N $$Yp = \left[ N - \sum_{i=0}^{N} (n-i) \cdot \frac{q^i \cdot \exp(-q)}{i} + N \right] \cdot \frac{1}{q} \quad (5)$$

where $$q = Rc \cdot Yt \cdot t_p \cdot N$$

The turnover time of photochemistry $t_p$ determines how fast electrons will be taken from the plastoquinone pool and used for photochemistry. The size of the plastoquinone pool N determines the maximum length of the electron queue waiting to be served. Eqn. 5 describes the fraction of electrons arriving at QA that can be served by photochemistry operating at limiting rate $1/t_p$. As long as the rate of charge separation is lower than photochemistry rate, the yield of photochemistry Yp is close to one. If the rate of charge separation exceeds the photochemistry rate, then the excess of electrons will be dissipated in the process of back-reaction or electron cycling around PSII, and the yield of the photochemistry will decrease. The yield of photochemistry is a mild function of the size of the plastoquinone pool N. Changes in N from 10 to 20 (the range of PQ pool size in algae) causes only 4% relative variability in the yield of photochemistry Yp at Rc=1, and much less at Rc different from 1. The absorption cross section $\sigma$PSII is measured as described in 3b. The average turnover time of water splitting for various species is relatively constant, and can be assumed to be about 200 $\mu$s. The knowledge of the turnover time of photochemistry $t_p$ is not necessary for the subsaturating irradiance levels. For the supersaturating irradiance levels, when the yield of photochemistry Yp is lower than 1, the $t_p$ parameter may be estimated from the measurement of the decay kinetics of variable fluorescence as described in 3.c, or from relation between the measured $\Delta\phi_{sat}$ and I.$\sigma$PSII. The irradiance level I is measured by the PAR sensor.

The parameter k in Eqn. 1 is described as $$k = a \cdot N_{II} \cdot \Delta\phi_{sat} \quad (6)$$

The parameter a is a stoichiometric coefficient describing the required number of photons absorbed by PSII per atom of carbon fixed and it ranges from 10 to 12. $N_{II}$ is the concentration of reaction centers and can be estimated from the intensity of the fluorescience signals Fp or Fs. The parameter $\Delta\phi_{sat}$ is calculated from Fs, Fp, and Fo fluorescence yield recorded by the two-chamber submersible fluorometer, as described in 3.a. The $\Delta\phi_{sat}$ characterizes the photosynthetic capacity of measured species, and is strongly dependent on the nutrient regime, changing from 0.3 to 1.7.

Figure 12:
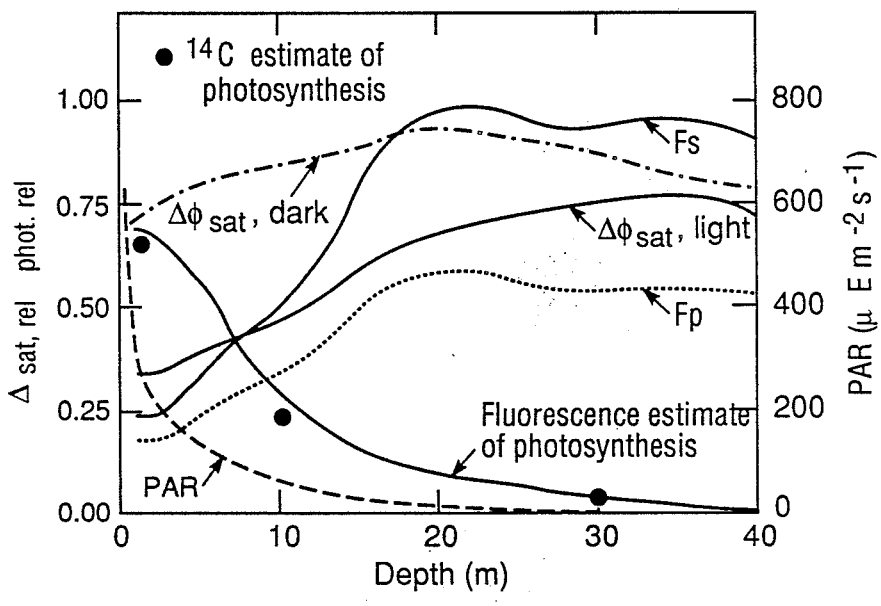
FIG. 12 illustrates an example of the fluorescence estimation of production rates in the sea, in situ, as compared wit the 14C method.

The example of the fluorescence estimation of production rates in the sea, in situ as compared with the 14C method, is presented in FIG. 12.

3e. Estimation of the Nutrient Regime and Normalized Growth Rate of Phytoplankton in the Ocean Both the range of variability of fluorescence yield in phytoplankton, $\Delta\phi_{sat}$, and the relative growth rate of the phytoplankton, are functions of nutrient availability. Accordingly, there is a relationship between $\Delta\phi_{sat}$ and growth rate. This relationship has been found to have a form $$\Delta\phi_{sat} = \Delta\phi_{max} \cdot [1 - \exp(-k \cdot \mu/\mu_{max})],$$

where $\Delta\phi_{sat}$ is the actual measured parameter, as described in subsection 3a., which depending on the nutrient conditions varies from 0.3 to 1.7, and $\Delta\phi_{max}$ is the same parameter for species grown under nutrient-replete conditions, ranging from 1.5 to 1.7. The $\mu/\mu_{max}$ is the relative growth rate under the actual nutrient conditions ranging from 0 to 1. The parameter k is very little species specific, and averages 3.5.

The measurement of $\Delta\phi_{sat}$ is done using either the double-chamber version of the submersible fluorometer, or using the non-submersible fluorometer. In the latter case only the discrete depths will be characterized.

A comparison between relative growth rate of phytoplankton as estimated with the disclosed method, and the chlorophyll concentration as recorded in the Gulf of Maine is presented in FIG. 13. The growth rate in relation to depth is shown in the upper chart, while chlorophyll concentration in relation to depth is shown in the lower chart of FIG. 13.

C. Sample Computer Program for Control of the Fluorometer

```
  1 REM
  2 REM   definition of the communication parameters between SBC and
         terminal
  3 REM   and host computer
  4 REM
 10 MTOP=3FFFH
 20 BAUD 9600
 21 REM
 22 REM   definition of the interrupt service for analog/digital conversion
 23 REM   and data acquisition
 24 REM
 30 STRING 165,80
 40 XBY(0C803H)=128
 50 XBY(4003H)=2 : XBY(4004H)=40H : XBY(4005H)=76H
 60 L=1  70 DBY(3EH)=6DH
 80 FOR N=1 TO 88
 90 READ D : XBY(16463+N)=D
100 NEXT N
110 DATA 043H,0D0H,018H,078H,04DH,079H,0E7H,07AH
120 DATA 0E6H,0ABH,020H,090H,0E0H,08DH,074H,008H
130 DATA 0F0H,074H,000H,0F0H,0BBH,000H,0FDH,053H
140 DATA 0D0H,0E7H,022H,000H,000H,000H,000H,000H
150 DATA 075H,0A8H,000H,043H,0D0H,018H,074H,000H
160 DATA 089H,083H,075H,082H,000H,0F0H,08AH,083H
170 DATA 0F0H,01BH,07CH,005H,0DCH,0FEH,089H,083H
180 DATA 075H,082H,000H,0E0H,0F6H,008H,075H,082H
190 DATA 001H,0E0H,0F6H,008H,08AH,083H,075H,082H
200 DATA 000H,0E0H,0F6H,008H,075H,082H,001H,0E0H
210 DATA 0F6H,008H,0D0H,0D0H,032H,000H,000H,000H
220 PRINT CHR(27),"[","1",";","24",CHR(72H)
230 PRINT CHR(27),"[","2","J",CHR(27),"[","20","A"
231 REM
232 REM   start of the menu-driven interface for programming the fluorometer
233 REM
240 PRINT  SPC (20),"**** FLUOROMETER CONTROL PROGRAM ****"
250 PRINT: PRINT "UP TO 60 DATA POINTS"
260 XBY(0E100H)=0 : XBY(0E200H)=0
270 REM ...DATA INPUT SECTION
280 PRINT CHR(27),"[","5","B"
281 REM
282 REM   entering the identification header that will be stored altogether
283 REM   with data in data file
284 REM
290 INPUT "EXPERIMENT ID :    ",$(1)
291 REM
292 REM   presetting the number of experiments to be executed
293 REM
300 PRINT : PRINT
310 INPUT "NO OF EXPERIMENTS :     ",N9
320 FOR I=1 TO N9
```

```
330 REM
331 REM  presetting the parameters for the i-th experiment
332 REM
340 PRINT  :  PRINT  SPC (10),"CONTROL DATA FOR ",I," EXPERIMENT"
350 PRINT "----------"
351 REM
352 REM  presetting number of flashes in a single cycle
353 REM
360 INPUT "NO OF FLASHES :          ",N(I)
363 REM
364 REM  presetting the length of a series in i-th experiment
365 REM
370 INPUT "NO OF DATA POINTS :      ",P(I)
371 REM
372 REM  presetting the number of repetition of every cycle
373 REM
380 INPUT "NO OF SHOTS :            ",S(I)
390 PRINT "----------"
391 REM
392 REM  presetting the duration of a cycle, intensity of the first probe
393 REM  flash and time delay between triggering the first probe flash
394 REM  and start of conversion
395 REM
400 INPUT "CYCLE LENGTH AND CYCLE INCREMENT [SEC]:      ",C(I),C1(I)
410 INPUT "FIRST FLASH INTENSITY AND INCREMENT [%]:     ",I1(I),M1(I)
420 INPUT "SAMPLE DELAY AND DELAY INCREMENT [USEC]:     ",G1(I),G4(I)
430 PRINT "----------"
440 IF N(I)=1 THEN  560
441 REM
442 REM  presetting the delay between the first probe flash and the
443 REM  pump flash, energy of the pump flash, and start of conversion
444 REM
450 INPUT "SECOND FLASH DELAY AND DELAY INCREMENT [MSEC]: ",D2(I),D4(I)
460 INPUT "SECOND FLASH INTENSITY AND INCREMENT [%]:      ",I2(I),M2(I)
470 INPUT "LINEAR OR LOGARYTHMIC (LI OR LO)?              ",$(0)
480 IF ASC($(0),2)=73 THEN Y2(I)=1
490 IF ASC($(0),2)=79 THEN Y2(I)=2
500 INPUT "SAMPLE DELAY AND DELAY INCREMENT [USEC]:       ",G2(I),G5(I)
510 PRINT "----------"
520 IF N(I)=2 THEN  560
551 REM
552 REM  presetting the delay time between the pump and second probe flash,
553 REM  energy of the second probe flash, and start of conversion
554 REM
530 INPUT "THIRD FLASH DELAY AND DELAY INCREMENT [MSEC]: ",D3(I),D5(I)
540 INPUT "LINEAR OR LOGARITHMIC (LI OR LO)?             ",$(0)
550 IF ASC($(0),2)=73 THEN Y1(I)=1
560 IF ASC($(0),2)=79 THEN Y1(I)=2
570 INPUT "THIRD FLASH INTENSITY AND INCREMENT [%]:      ",I3(I),M3(I)
580 INPUT "SAMPLE DELAY AND DELAY INCREMENT [USEC]:      ",G3(I),G6(I)
590 INPUT "NUMBER OF PRE-FLASHES AND INCREMENT:          ",B1(I),B4(I)
600 INPUT "TIME DELAY FOR PREFLASHES AND INCREMENT [MS]: ",B2(I),B5(I)
```

```
610 INPUT "PROBE FOR DELTA CALCULATIONS AND INCREMENT:       ",B3(I),B6(I)
620 INPUT "....IS THAT OK?   ",$(0)
630 IF ASC($(0),1)<>89 THEN  320
640 NEXT I
641 REM
642 REM   presetting the time delay between experiments
643 REM
650 INPUT "TIME DELAY BETWEEN EXPERIMENTS [MIN]:         ",T4
660 G9=0
670 REM
671 REM   determining if the fluorescence yield during the pump flash is
672 REM   to be recorded.  If yes, modification of the interrupt service
673 REM   for data conversion and storing
674 REM
680 INPUT "RECORD DATA AT PUMP FLASH?   ",$(0)
690 IF ASC($(0),1)=89 THEN 750
700 FOR N=1 TO 16
710 READ D : XBY(16545+N)=D
720 NEXT N
730 DATA 090H,0E0H,08DH,0B8H,051H,004H,074H,001H
740 DATA 070H,002H,074H,000H,0F0H,0D0H,0D0H,032H
750 G9=1
760 REM
761 REM   dialog with the operator (only bench-top fluorometer)
762 REM
770 INPUT "SWITCH ON THE HIGH VOLTAGE !",$(0)
780 INPUT "ARE YOU READY?   ",$(0)
790 IF ASC($(0),1)<>89 THEN  710
800 CLOCK1
810 XBY(0C800H)=255
820 XBY(0C800H)=0
830 REM
831 REM   general initialization
832 REM
840 T=1/3000 : T3=1/3 : N0=N
850 TIME=0
860 DIM O3(60),O5(60),O6(60),O7(60),O8(60) 870 DIM O9(60)
871 REM
872 REM   start of the fluorometer operation
873 REM
880 FOR I=1 TO N9 :   REM ....INITIALIZATION SECTION
881 REM
882 REM initialization for the i-th experiment
883 REM
890 P1=0E100H: P2=0E200H: P3=0E300H: P4=0E400H: P5=0E500H: P6=0E600H
900 P7=0E700H : A=0E080H : B=0E000H
910 XBY(B+0AH)=0 : XBY(B+0BH)=0 : XBY(B+0CH)=0
920 XBY(A)=0 : XBY(A)=2 : XBY(A+1)=0F4H
930 XBY(A+2AH)=10H : XBY(A+2BH)=46H : XBY(A+5)=1 : XBY(A+6)=4
940 XBY(B)=0 : XBY(B)=2 : XBY(B+1)=0F4H
950 XBY(B+2AH)=11H : XBY(B+2BH)=64H
960 XBY(B+0DH)=0FBH
```

```
970  D2=D2(I) : D3=D3(I) : D4=D4(I) : D5=D5(I)
980  C=C(I) : C1=C1(I) : I1=I1(I) : I2=I2(I) : I3=I3(I)
990  M1=M1(I) : M2=M2(I) : M3=M3(I) : P=P(I) : S=S(I) : N4=N(I)
1000 G1=G1(I) : G2=G2(I) : G3=G3(I) : G4=G4(I) : G5=G5(I) : G6=G6(I)
1010 B1=B1(I) : B2=B2(I) : B3=B3(I) : B4=B4(I) : B5=B5(I) : B6=B6(I)
1020 Q9=0 : Y1=Y1(I) : Y2=Y2(I)
1030 DBY(20H)=N4
1040 IE=IE.OR.81H
1041 REM
1042 REM  terminal screen initialization (bench-top fluorometer), if
1043 REM  terminal present
1044 REM
1050 PRINT CHR(27),"[","2","J"
1060 PRINT CHR(27),"[","1",";","24","H","*** EXPERIMENT NO ",I," ***"
1070 PRINT "DATA POINT", SPC (16),"SHOT NO"
1080 P."FLASH 1 INT.", SPC (14),"CYCLE LENGTH", SPC (18),"SAMP 1 DELAY"
1090 IF N4=1 THEN 1130
1100 P."FLASH 2 INT.", SPC (14),"FLASH 2 DELAY", SPC (17),"SAMP 2 DELAY"
1110 IF N4=2 THEN 1130
1120 P."FLASH 3 INT.", SPC (14),"FLASH 3 DELAY", SPC (17),"SAMP 3 DELAY"
1130 PRINT CHR(27),"[","6",";","1","H"
1140 PRINT "    CYCLE    DELAY 2    DELAY 3     EX1      EM1      EX2"
1150 PRINT CHR(27),"[","7",";","54","H","    EM2      EX3      EM3"
1160 PRINT CHR(27),"[","9",";","24",CHR(72H)
1170 FOR I5=1 TO P : REM ....DATA POINT
1180 K=31190 IF G2/1000>D3 THEN K=2
1200 T1=D3/T : N1=0.5
1210 DO : N1=N1*2 : T2=T1/N1 :   UNTIL T2<65536
1220 N3=D3/(N1*T)
1230 PRINT CHR(27),"[","2",";","13","H",USING(##),I5
1240 PRINT CHR(27),"[","3",";","14","H",USING(##.#),I1
1250 PRINT CHR(27),"[","3",";","43","H",C
1260 PRINT CHR(27),"[","3",";","71","H",G1
1270 IF N4=1 THEN 1350
1280 PRINT CHR(27),"[","4",";","14","H",I2
1290 PRINT CHR(27),"[","4",";","43","H",D2
1300 PRINT CHR(27),"[","4",";","71","H",G2
1310 IF N4=2 THEN 1350
1320 PRINT CHR(27),"[","5",";","14","H",I3
1330 PRINT CHR(27),"[","5",";","43","H",D3
1340 PRINT CHR(27),"[","5",";","71","H",G3
1350 REM
1360 REM loading the "first probe conversion start" timer with preset
1361 REM value
1362 REM
1370 X2=INT(G1/T3) : X0=X2 :  IF X2<1 THEN X2=1 : XBY(A+16H)=0
1380 IF X2<256 THEN 1400
1390 X1=INT(X2/256) : X0=X2-256*X1 : XBY(A+16H)=X1
1400 XBY(A+17H)=X0 : XBY(A+1CH)=50H : XBY(A+0AH)=4
1401 REM
1402 REM  loading the "delay between first probe and pump" timer with the
1403 REM  preset value
1410 REM
```

```
1420 IF N4=1 THEN 1670
1430 N2=INT(D2/0.021333)
1440 X0=N2 : XBY(A+18H)=0 :  IF N2<256 THEN 1460
1450 X1=INT(N2/256) : X0=N2-256*X1 : XBY(A+18H)=X1
1460 XBY(A+19H)=X0 : XBY(A+1DH)=70H : XBY(A+0BH)=4
1461 REM
1462 REM  loading the "pump conversion start" timer with preset value
1470 REM
1480 X2=INT(G2/T3) : X0=X2 :  IF X2<1 THEN X0=1 : XBY(A+1AH)=0
1490 IF X2<256 THEN 1510
1500 X1=INT(X2/256) : X0=X2-256*X1 : XBY(A+1AH)=X1
1510 XBY(A+1BH)=X0 : XBY(A+1EH)=50H : XBY(A+0CH)=4
1520 IF N4=2 THEN 1620
1521 REM
1530 REM  loading the "delay between the pump and second probe" timer
1531 REM  with preset value
1532 REM
1540 X0=N3 : XBY(B+16H)=0 :  IF N3<256 THEN 1560
1550 X1=INT(N3/256) : X0=N3-256*X1 : XBY(B+16H)=X1
1560 XBY(B+17H)=X0 : XBY(B+1CH)=50H : XBY(B+0AH)=4
1570 REM
1571 REM  loading the "second probe conversion start" timer with preset
1572 REM  value
1573 REM
1580 X2=INT(G3/T3) : X0=X2 :  IF X2=0 THEN X0=1 : XBY(B+18H)=0
1590 IF X2<256 THEN 1610
1600 X1=INT(X2/256) : X0=X2-256*X1 : XBY(B+18H)=X1
1610 XBY(B+19H)=X0 : XBY(B+1DH)=50H : XBY(B+0BH)=4
1620 REM
1621 REM  loading the prescaler timer (for generation of time delay longer
1622 REM  than 24 ms)
1623 REM
1630 IF N1=1 THEN 1680
1640 X0=N1 : XBY(B+1AH)=0 :  IF N1<256 THEN 1660
1650 X1=INT(N1/256) : X0=N1-256*X1 : XBY(B+1AH)=X1
1660 XBY(B+1BH)=X0 : XBY(B+1EH)=0C0H : XBY(B+0CH)=6 : XBY(B+1CH)=70H
1661 REM
1670 REM  loading the D/A converters controlling the energy of the pump
         flash and probe flashes
1672 REM
1673 REM
1680 XBY(P1)=0 : XBY(P2)=0
1690 CLOCK 0
1700 CALL 4050H
1710 CLOCK 1
1720 N5=INT(I1*2.55) : N6=INT(I2*2.55)
1730 IF N5>255 THEN N5=255 :  IF N6>255 THEN N6=255
1740 C9=C-0.001*(D2+D3)
1750 A0=0 : A1=0 : A2=0 : A3=0 : A8=0 : A9=0
1760 XBY(B+0DH)=0
1770 XBY(P1)=N5 : XBY(P2)=N6
```

```
1780 I7=INT(S/4)+1 :   FOR I8=1 TO I7
1790 Q9=TIME+C9
1800 IF TIME<Q9 THEN 1800
1801 REM
1802 REM   execution of a single cycle with probe flashes not fired for
1803 REM   measuring of the dark signals, estimation of the effect of the
1804 REM   tail of the pump flash, and estimation of the luminescence signal
1805 REM
1806 REM
1810 CLOCK 0 :   CALL 4050H :   CLOCK 1
1820 Z1=(DBY(4DH)*16+DBY(4EH)/16)/40.95
1830 Z2=(DBY(51H)*16+DBY(52H)/16)/40.95
1840 Z3=(DBY(55H)*16+DBY(56H)/16)/40.95
1850 A1=Z1+A1 : A2=Z2+A2 : A3=Z3+A3
1860 A0=Z1*Z1+A0 : A8=Z2*Z2+A8 : A9=Z3*Z3+A9
1870 NEXT I8
1880 A1=A1/I7 : A2=A2/I7 : A3=A3/I7
1890 A8=SQR(ABS(A8/I7-A2*A2)) : A9=SQR(ABS(A9/I7-A3*A3))
1900 A8=A8/SQR(I7+0.001) : A9=A9/SQR(I7+0.001)
1910 A0=SQR(ABS(A0/I7-A1*A1)) : A0=A0/SQR(I7+0.001)
1920 XBY(B+0DH)=41930 A4=0 : A5=0 : A6=0 : A7=0
1940 CLOCK 0
1950 FOR I8=1 TO 4
1960 CALL 4050H
1970 Z1=(DBY(4FH)*16+DBY(50H)/16)/40.95
1980 Z2=(DBY(53H)*16+DBY(54H)/16)/40.95
1990 Z3=(DBY(57H)*16+DBY(58H)/16)/40.95
2000 Z4=(DBY(51H)*16+DBY(52H)/16)/40.95
2010 A4=Z1+A4 : A5=Z2+A5 : A6=Z3+A6 : A7=Z4+A7
2020 NEXT I8
2030 A4=A4/4 : A5=A5/4 : A6=A6/4 : A7=A7/4
2040 IF G9=1 THEN A2=A7
2050 CLOCK 1
2060 PRINT "DARK SIGNALS :    ",USING(#.#),A4,A1,A0,A5,A2,A8,A6,A3,A9
2070 XBY(B+0DH)=0FBH
2080 U1=0 : U2=0 : U3=0 : U4=0 : U5=0 : U6=0
2090 U7=0 : U8=0 : U9=0
2100 F4=0 : F5=0 : F6=0 : E4=0 : E5=0 : E6=0
2110 E1=0 : E2=0 : E3=0 : F1=0 : F2=0 : F3=0
2120 S1=0 : S2=0 : S3=0 : S4=0 : S5=0 : S6=0
2130 V1=0 : V2=0 : V3=02140 C8=(D2+D3)*0.001
2150 C9=C8+G1*0.00000
12160 IF N4>1 THEN C9=G2*0.000001+C9
2170 IF N4>2 THEN C9=G3*0.000001+C9
2180 C0=B2*0.001-C9-0.0112190 C9=C-C9-0.011
2200 XBY(0C800H)=255
2210 IF TIME<Q2 THEN 2210
2220 XBY(0C800H)=0
2221 REM
2222 REM   excution of the measurement cycle
2223 REM
2230 FOR I6=1 TO S :   REM ....SHOT
```

```
2240 IF TIME<Q2 THEN 2240
2250 XBY(0C800H)=02260 XBY(P1)=N5 : XBY(P2)=N6
2270 PRINT CHR(27),"[","2",";","39","H",USING(####),I6
2280 PRINT CHR(27),"[","23",";","1","H"
2290 N2=INT((D2+rnd*200)/0.021333)
2300 X0=N2 : XBY(A+18H)=0 :  IF N2<256 THEN 2320
2310 X1=INT(N2/256) : X0=N2-256*X1 : XBY(A+18H)=X1
2320 XBY(A+19H)=X0 : XBY(A+1DH)=70H : XBY(A+0BH)=4
2330 IF TIME<Q9 THEN 2330
2340 Q9=TIME+C9
2350 CLOCK 0
2360 CALL 4050H
2370 CLOCK 1
2371 REM
2372 REM   retrieving the data from address space used by interrupt
2373 REM   service into system variables
2374 REM
2380 F1=(DBY(4DH)*16+DBY(4EH)/16)/40.95
2390 E1=100
2400 F1=-A1+F12410 XBY(0C800H)=255
2420 F2=(DBY(51H)*16+DBY(52H)/16)/40.95
2430 E2=1002440 F2=-A2+F2
2450 F3=(DBY(55H)*16+DBY(56H)/16)/40.95
2460 E3=100
2470 F3=-A3+F3
2480 F4=F1+F4 : E4=E1+E4 : S1=F1*F1+S1 : S2=E1*E1+S2
2490 F5=F2+F5 : E5=E2+E5 : S3=F2*F2+S3 : S4=E2*E2+S4
2500 F6=F3+F6 : E6=E3+E6 : S5=F3*F3+S5 : S6=E3*E3+S6
2510 PRINT USING(###.##),C,D2,D3,USING(###.###),E1,F1,E2,F2,E3,F3
2520 NEXT I6
2530 IF TIME<Q2 THEN 2530
2540 XBY(0C800H)=0
2550 Y=SQR(S)
2551 REM
2552 REM   averaging of the probe excitation signals
2553 REM
2560 E4=E4/S : E5=E5/S : E6=E6/S
2570 S2=SQR(ABS(S2/S-E4*E4))
2580 S4=SQR(ABS(S4/S-E5*E5))
2590 S6=SQR(ABS(S6/S-E6*E6))
2600 S2=S2/Y : S4=S4/Y : S6=S6/Y
2610 PUSH E4 :   GOSUB 3220 :   POP E4
2611 REM
2622 REM   linearization of the probe excitation signals
2623 REM
2630 IF G9=0 THEN 2660
2640 PUSH E6 :   GOSUB 3220 :   POP E6
2650 GOTO 2680
2660 PUSH E5 :   GOSUB 3220 :   POP E5
2670 PUSH E6 :   GOSUB 3220 :   POP E6
2680 REM
2690 PRINT USING(###.##),CHR(27),"[","1"
```

```
2700 REM
2701 REM   statistical analysis of the fluorescence yield signals
2702 REM
2710 F4=F4/S : F5=F5/S : F6=F6/S
2720 S1=SQR(ABS(S1/S-F4*F4))
2730 S1=SQR(ABS(S1*S1+A0*A0))
2740 S3=SQR(ABS(S3/S-F5*F5))
2750 S3=SQR(ABS(S3*S3+A8*A8))
2760 S5=SQR(ABS(S5/S-F6*F6))
2770 S5=SQR(ABS(S5*S5+A9*A9))
2780 S1=S1/Y : S3=S3/Y : S5=S5/Y
2790 U4=100*F4/(E4+0.001): U5=100*F5/(E5+0.0001): U6=100*F6/(E6+0.001)
2800 E4=0.001+E4 : E5=0.001+E5 : E6=0.001+E6
2810 U7=SQR((S1/E4)**2+(S2*F4/(E4*E4))**2)
2820 U8=SQR((S3/E5)**2+(S4*F5/(E5*E5))**2)
2830 U9=SQR((S5/E6)**2+(S6*F6/(E6*E6))**2)
2840 U7=100*U7 : U8=100*U8 : U9=100*U9
2850 IF K=2 THEN V2=(U5-U4)/(U4+0.001)
2860 IF K=3 THEN V2=(U6-U4)/(U4+0.001)
2870 IF K=2 THEN V3=SQR((U8/U4)**2+(U7*U5/(U4*U4))**2)
2880 IF K=3 THEN V3=SQR((U9/U4)**2+(U7*U6/(U4*U4))**2)
2890 IF ABS(U4)>999 THEN U4=999 :   IF ABS(U7)>999 THEN U7=999
2900 IF ABS(U5)>999 THEN U5=999 :   IF ABS(U8)>999 THEN U8=999
2910 IF ABS(U6)>999 THEN U6=999 :   IF ABS(U9)>999 THEN U9=999
2911 REM
2912 REM   printing of data for a single cycle, if printer present
2923 REM
2920 PRINT USING(###.##),CHR(27),"[","1"
2930 PRINT USING(###.##),U4,U6,"              ",V2,V3
2931 REM
2932 REM   modification of control parameters for the next cycle in series
2933 REM
2940 O3(I5)=D3:O5(I5)=I2
2950 O6(I5)=U4:O7(I5)=U6:O8(I5)=V2:O9(I5)=V3
2960 C=C1+C : I1=M1+I1 : I3=M3+I3 : D2=D4+D2
2970 G1=G4+G1 : G2=G5+G2 : G3=G6+G3
2980 B1=B4+B1 : B2=B5+B2 : B3=B6+B3
2990 IF Y1=1 THEN D3=D5+D3
3000 IF Y1=2 THEN D3=(10**D5)*D3
3010 IF Y2=1 THEN I2=M2+I2
3020 IF Y2=2 THEN I2=(10**M2)*I2
3030 NEXT I5
3031 REM
3032 REM   end of the single experiment
3032 REM
3035 REM   Transfer of data to a host computer
3036 REM
3036 PRINT "TRANSFERRING"
3040 P.# $(1)
3050 PRINT USING(####)
3060 P.# "NO OF PUMP FLASHES:     ",B1(I),B4(I)
3070 P.# "PROBE ACQUIRED:         ",B3(I),B6(I)
```

```
3080 PRINT USING(####)
3090 P.# "TIME DELAY BETWEEN PUMPS:   ",B2(I),B5(I)
3100 FOR K=1 TO P
3110 A1=C:A2=D2:A3=O3(K):A4=I1:A5=O5(K):A6=O6(K)
3120 A7=O7(K):A8=O8(K):A9=O9(K)
3130 P.# USING(###.##),A1,USING(###.###),A2,A3,A4,A5,A6,A7,A8,A9
3131 REM
3132 REM   go to execution of the next experiment
3133 REM
3140 NEXT K
3150 IF I=N9 THEN PRINT# "$" ELSE PRINT# "*"
3155 GOTO 3035
3160 Q2=TIME+T4*60
3170 IF TIME<Q2 THEN 3170
3180 NEXT I
3190 PRINT "END OF THE PROGRAM"
3200 END
3201 REM
3202 REM   end of the programs
3203 REM
3210 REM    *SUB* PROBE EX LINEARIZATION
3220 POP X
3230 IF X<=4.7 THEN X=0.45*X
3240 IF X>4.7.AND.X<=10.45 THEN X=X*(0.45+0.04*(X-4.7)/5.75)
3250 IF X>10.45.AND.X<=21.94 THEN X=X*(0.49+0.17*(X-10.45)/11.49)
3260 IF X>21.94.AND.X<=35.40 THEN X=X*(0.66+0.142*(X-21.94)/13.46)
3270 IF X>35.40.AND.X<=56.96 THEN X=X*(0.802+0.108*(X-35.40)/21.56)
3280 IF X>56.96 THEN X=X*(0.91+0.09*(X-56.96)/34.99)
3290 PUSH X
3300 RETURN
3310 REM $$$$$$$$$$$$$$$$$$$$$
```

We claim:

1. A computer controlled fluorometer device for conveniently making rapid and accurate measurements of plant or phytoplankton photosynthetic parameters including ranges of variable fluorescence, $\Delta\phi_{sat}$, absorption cross section, $\sigma(PSII)$, decay kinetics of variable fluorescence, and levels of energy transfer between PSII units in either essential darkness or under background illumination, comprising:

(a) a pump flash source, a probe flash source, a sample chamber having a cavity for containing a sample of plant or phytoplankton to be measured, a programmable computer means including a microprocessor, and data and address bus means and D/A converters for operatively connecting said computer means to enable the computer means when programmed to control energy, increment, repetition, and sequencing of both said pump flash source and said probe flash source;

(b) light filter, collimator, and reflector means arranged in operating relationship between said pump flash source and the sample chamber, and between said probe flash source and the sample chamber, for directing pump flashes and probe flashes, produced, respectively, by said flash sources, into the sample chamber;

(c) a light condenser lens system, emission filters, and a fluorescence detector with a photomultiplier (PMT) arranged in series to collect light emitted from said sample chamber and direct it into the PMT, said PMT being operable to produce a signal that corresponds to said light directed into the PMT, the operation of said PMT being controlled by a power supply that is operably connected to it and to said computer means from which control signals are transmitted to the power supply;

(d) signal conditioning unit and two flash monitoring means, each operatively connected, respectively, to monitor pump flash light each probe flash light generated by said flash sources, said monitoring means being further operably connected to transmit signals corresponding to said monitored flashes to said signal conditioning unit, said signal conditioning unit being operably connected to be controlled by, and to transmit signals to, said microprocessor;

(e) a software programmable source of background irradiance, said programmable source being operably connected to receive programmed signals from said microprocessor, and being arranged to emit light into said sample chamber; and (f) a computer program installed to run said microprocessor, thereby to control the operation of said flash sources, said power supply controlling the PMT, and said signal control unit, to enable the fluormeter device to make said measurements, said computer program being further operable to control said computer means to collect, analyze, and store data relating to said measurements.

2. A fluorometer device as defined in claim 1 including a peristaltic pump that allows said measurements to be made in a flow-through system, and a relay operatively connected to said pump and to said microprocessor, said relay being operable under the control of said computer program to control the flow of fluid through said pump.

3. A fluorometer device as defined in claim 1 including a submersible temperature sensor, a depth sensor, and a photosynthetic active radiation (PAR) sensor, and converter amplifier, a multiplexer, programmable gain amplifier and analog to digital (A/D) converter operably connected to feed signals from said sensors to said microprocessor and to said source of background irradiance, said multiplexer, programmable gain amplifier, and A/D converter also being operably connected to said microprocessor for receiving programmed control signals from the microprocessor.

4. A method of operating a computer controlled fluorometer device as defined in claim 1 to measure the fluorescence yield of PSII as the ratio of the fluorescence signal to the excitation signal under a condition that prevents the excitation signal from changing the state of the reaction centers, comprising the steps of controlling the probe flash produced by the probe flash source in the device so that the integrated number of excitation photons emitted during each probe flash is kept small enough to prevent any reaction center from being hit more than once.

5. A method as defined in claim 4 including the step of keeping the probe flash energy of each controlled probe flash below 1% of the energy of the saturating pump flash, and keeping the duration of the probe flash exposition shorter than the time constant of $QA^-$ oxidation so the duration is about 160 microseconds.

6. A method of operating a computer controlled fluorometer device as defined in claim 1 to produce a predetermined series of probe/pump cycles of pre-programmed parameters, including the step of producing at least one pump flash and at least two probe flashes, with the probe flashes being produced before and after the pump flash in the series.

7. A method as defined in claim 6 including the step of making the pre-progammed parameters include duration of predetermined series cycle, energy of the probe and pump flashes, time delay between the flashes, and energy of the flashes.

8. A method as defined in claim 7 including the step of making the pre-progammed parameters include increment factor of each probe flash, and determination of any change in the increment factor from cycle to cycle in the series.

9. A computer controlled florometer device as defined in claim 1 including a second sample chamber arranged in operating relationship to said light filter, collimator, and reflector means to receive into said second chamber pump flashes and probe flashes.

10. A method of operating the device defined in claim 9 comprising placing a dark adapted sample into said second chamber, pre-progamming the computer means to produce a predetermined series of flashes that include a probe flash during which the amplitude of the minimal fluorescence yield Of from the sample is recorded in the computer means, further pre-programming the computer means to produce a pump flash several milliseconds after the probe flash and applying it at saturating intensity to said sample, and further applying a second probe flash to the sample within 50 to 70 microseconds after the pump flash while the reaction centers of the sample are closed, thereby to provide data for use in calculating selected photosynthetic parameters.

11. A method as defined in claim 10 including the step of pre-programming the computer means to repeat the cycle of probe-pump-probe flashes several times at preset intervals between each cycle.

12. A method as defined in claim 11 including further pre-programming said computer means to gradually increase the intensity of each succeeding pump flash in the series of repeated cycles.

13. A method as defined in claim 12 including making the initial pump flash in the pre-programmed series be at essentially saturation level.

14. A method of operating the device defined in claim 9 to measure the decay kinetics of the fluorescence yield of a sample including pre-programming the computer means to produce a predetermined series of probe-pump-probe flash cycles, and further pre-programming the computer means to keep the intensity of each pump flash at saturating level, and making the pre-programming effective to operate the device to gradually increase the delay between the pump flash and the second probe flash from about 50 microseconds to a predetermined required time period.

* * * * *